United States Patent
Kim et al.

(10) Patent No.: US 11,890,364 B2
(45) Date of Patent: Feb. 6, 2024

(54) COMPOSITION FOR PREVENTION OR TREATMENT OF HAIR LOSS

(71) Applicant: GOOD T CELLS, INC., Seoul (KR)

(72) Inventors: Beom Seok Kim, Seoul (KR); Jung Ho Kim, Seoul (KR)

(73) Assignee: Good T Cells, Inc., Seoul (KR)

(*) Notice: Subject to any disclaimer, the term of this patent is extended or adjusted under 35 U.S.C. 154(b) by 89 days.

(21) Appl. No.: 16/768,051

(22) PCT Filed: Dec. 3, 2018

(86) PCT No.: PCT/KR2018/015202
§ 371 (c)(1),
(2) Date: May 28, 2020

(87) PCT Pub. No.: WO2019/108047
PCT Pub. Date: Jun. 6, 2019

(65) Prior Publication Data
US 2020/0352839 A1    Nov. 12, 2020

(30) Foreign Application Priority Data
Dec. 1, 2017 (KR) .................. 10-2017-0164440

(51) Int. Cl.
| | | |
|---|---|---|
| *A61K 47/64* | (2017.01) | |
| *A61K 8/44* | (2006.01) | |
| *A61Q 7/00* | (2006.01) | |
| *C07K 19/00* | (2006.01) | |
| *C07K 7/08* | (2006.01) | |
| *A61K 45/06* | (2006.01) | |

(52) U.S. Cl.
CPC ............ *A61K 8/44* (2013.01); *A61K 47/64* (2017.08); *A61Q 7/00* (2013.01); *C07K 7/08* (2013.01); *C07K 19/00* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2009/0203574 A1 | 8/2009 | Fuchs et al. | |
| 2013/0028917 A1* | 1/2013 | Howard ............. | A61K 47/6855 424/178.1 |
| 2014/0186379 A1 | 7/2014 | Jo et al. | |
| 2015/0329847 A1 | 11/2015 | Lee | |
| 2019/0111141 A1 | 4/2019 | Lee | |
| 2020/0289526 A1 | 9/2020 | Chung | |

FOREIGN PATENT DOCUMENTS

| | | |
|---|---|---|
| KR | 10-1349300 | 2/2014 |
| KR | 10-2014-0060842 | 5/2014 |
| WO | WO 99-65483 | 12/1999 |
| WO | 2006/098422 A1 | 9/2006 |
| WO | WO 2016028036 | 2/2016 |
| WO | 2016/163806 A1 | 10/2016 |
| WO | 2017159922 A1 | 9/2017 |

OTHER PUBLICATIONS

Arnold et al, Increased levels of inflammatory cytokines in the female reproductive tract are associated with altered expression of proteases, mucosal barrier proteins, and an influx of HIV-susceptible target cells, Mucosal Immunology vol. 9, pp. 194-205 (2016) (Year: 2016).*
International Search Report dated May 11, 2019 for International Application No. PCT/KR2018/015202, 6 pages.
Poreba et al., "Caspase substrates and inhibitors," Cold Spring Harbor Perspectives in Biology, 5(8): a008680 (2013).
Julien et al., "Caspases and their substrates," Cell Death and Differentiation, 24, 1380-1389 (2017).
Song et al., "Cascleave: towards more accurate prediction of caspase substrate cleavage sites," Bioinformatics, 26(6), 752-760 (2010).
Bao et al., "Toward more accurate predicition of caspase cleavage sites: a comprehensive review of current methods, tools and features," Briefings in Bioinformatics, 20(5), 1669-1684 (2019).
Cunningham et al., "Caspase activation in hair cells of the mouse utricle exposed to neomycin," The Journal of Neuroscience, 22(19), 8532-8540 (2002).
*Erfindergemeinschaft UroPep GbR* v. *Eli Lilly & Co.*, 276 F.Supp.3d 629 (E.D. Tex. 2017), aff'd, 739 F. App'x 643 (Fed. Cir. 2018).
Q.U. Ain et al., "Effects of protein transduction domain (PTD) selection and position for improved intracellular delivery of PTD-Hsp27 fusion protein formulations," Arch. Pharm. Res., 39(9), 1266-1274 (2016).
K.M. Wagstaff et al., "Protein Transduction: Cell Penetrating Peptides and Their Therapeutic Applications," Current Medicinal Chemistry, 13, 1371-1387 (2006).
L.L. Cunningham et al., "Caspase Activation in Hair Cells of the Mouse Utricle Exposed to Neomycin," J. Neuroscience, 22(19), 8532-40 (2002).
O. Julien & J.A. Wells, "Caspases and their substrates," Cell Death and Differentiation, 24, 1380-89 (2017).

* cited by examiner

*Primary Examiner* — Thomas S Heard
(74) *Attorney, Agent, or Firm* — McDonnell Boehnen Hulbert & Berghoff LLP

(57) ABSTRACT

The present invention relates to a composition for prevention or treatment of hair loss. The composition is effectively delivered into hair papilla cells in a hair loss area, which is a target area, wherein a cytokine or enzyme highly expressed in the hair loss area causes a drug to be separated from a compound contained in the composition so that the drug effectively exhibits activity, which ultimately promotes hair growth and/or hair regrowth.

11 Claims, 4 Drawing Sheets
Specification includes a Sequence Listing.

SEQUENCE LISTING

<160> NUMBER OF SEQ ID NOS: 8

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide

<400> SEQUENCE: 1

Tyr Gly Arg Arg Ala Arg Arg Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Tyr Ala Arg Val Arg Arg Arg Gly Pro Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Tyr Gly Arg Lys Lys Arg Arg Gln Arg Arg
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Tyr Val Ala Asp
1

<210> SEQ ID NO 5
<211> LENGTH: 3
<212> TYPE: PRT
<213> ORGANISM: Artificial Sequence
<220> FEATURE:
<223> OTHER INFORMATION: Synthetic peptide

<400> SEQUENCE: 5

Tyr Val Ala
1

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Tyr Gly Arg Arg Ala Arg Arg Arg Arg Arg Cys
1               5                   10

```
<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Tyr Ala Arg Val Arg Arg Arg Gly Pro Arg Arg Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Tyr Gly Arg Lys Lys Arg Arg Gln Arg Arg Cys
1               5                   10
```

COMPOSITION FOR PREVENTION OR TREATMENT OF HAIR LOSS

CROSS-REFERENCE TO RELATED APPLICATIONS

This application is a U.S. National Stage application of International Patent Application PCT/KR2018/015202, filed Dec. 3, 2018, which claims the benefit of priority of Korean Patent Application no. 10-2017-0164440, filed Dec. 1, 2017.

TECHNICAL FIELD

The present invention relates to a composition for prevention or treatment of hair loss.

BACKGROUND ART

For hair loss, genetic factors act as the most important cause. In recent years, however, the population with hair loss is gradually increasing due to increased social stress, as well as environmental pollution, westernized diet such as instant food, frequent perm and dyeing, and wrong scalp care.

Hair is maintained by repeating hair regrowth and hair loss following a cycle of growth phase (anagen), regression phase (catagen), and resting phase (telogen). Specifically, the cycle may be divided into the growth phase (anagen) during which hair grows, the regression phase (catagen) during which the hair ends growing and the hair bulb shrinks, the resting phase (telogen) during which the hair papilla stops working and keeps the hair on the scalp, and a new anagen phase during which the hair papilla begins to work or develops new hair so that the old hair is caused to fall out.

The anagen lasts 3 to 5 years for men and 4 to 6 years for women, followed by the catagen of about 30 to 45 days and the telogen of about 3 to 4 months. Then, the hair naturally falls out. At the end of the telogen, a new anagen phase, during which new hair is produced, begins.

Hair loss is a normal phenomenon. However, as compared with a normal person having a lot of hair at anagen, a person with alopecia usually has a lot of hair at telogen, which makes a hair loss phenomenon visible.

The characteristic of people who exhibit alopecia is miniaturization of hair. As hair loss progresses, the period of anagen is shortened, and thus the hair becomes smaller and smaller. Therefore, for the treatment of hair loss, it is important to allow hair follicles at telogen to enter anagen quickly and to increase the shortened period of anagen.

Androgenetic alopecia, which causes male sexual characteristics to develop, is a phenomenon manifested by the male hormone called testosterone, a hormone that acts on development of muscles, development of male organs, and the like during puberty. When this testosterone is converted to the more potent hormone, dihydrotestosterone (DHT), by an enzyme called 5-alpha reductase, the thus converted hormone acts on hair follicles so that the hair follicles are induced to go from anagen to catagen, thereby causing hair loss. Therefore, in order to treat alopecia caused by this, a method of inhibiting production of DHT caused by 5-alpha reductase is mainly used.

Alopecia areata is caused by an autoimmune disease, mental stress, or genetic predisposition. Alopecia areata causes round or oval patches of hair loss, and is characterized by tinea capitis or trichotillomania. Alopecia areata is fundamentally different from androgenetic alopecia in terms of cause. Also, a different treatment method such as adrenocortical hormone therapy is used for alopecia areata.

For such various and complicated causes of hair loss, as anti-hair loss products known to date, there are commercially available products that contain, as an active ingredient, an ingredient or the like for the purpose of promoting blood circulation, suppressing male hormonal action, reinforcing hair root function, or the like. However, in terms of effectiveness, there are no products that have a distinct effect; and the problem of side effects is also raised for most products.

Technical Problem

An object of the present invention is to provide a composition for various uses, including prevention or treatment of hair loss.

Another object of the present invention is to provide a method for preventing or treating hair loss.

Other objects and advantages of the present invention will become more apparent from the following detailed description, claims, and drawings.

Solution to Problem

According to an embodiment of the present invention, there is provided a compound represented by Formula 1:

$$P\text{-}W\text{-}L_1\text{-}M\text{-}A \qquad \text{[Formula 1]}$$

in Formula 1,

P is a protein transduction domain (PTD),

W is a direct bond or includes at least one amino acid, $L_1$ is a linker,

M is a direct bond or a linker represented by Formula 2, and

A is a drug for prevention or treatment of hair loss, $$*\text{-}X\text{-}L_2\text{-}* \qquad \text{[Formula 2]}$$

in Formula 2,

* is a site where a bond is formed,

X is a cleavage site, and $L_2$ is a linker.

In the present invention, the "protein transduction domain (PTD)" is a short peptide with strong hydrophobicity which consists of 7 to 50 amino acids, and refers to a domain capable of delivering, into cells, a protein having a molecular weight of 120 kDa or more as well as DNA or RNA.

In the present invention, for the protein transduction domain, any one selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP) may be used, or a macromolecule transduction domain disclosed in WO2016/028036A1 or US Laid-open Patent Application No. 2014-0186379 may be used. However, the present invention is not limited thereto, and any protein transduction domain, which is generally used in the art or commercially available, may be used without limitation. Preferably, the protein transduction domain may be CTP represented by SEQ ID NO: 1, Hph-1 represented by SEQ ID NO: 2, or Tat represented by SEQ ID NO: 3.

The terms "11R" and "7R" as used herein refer to peptides composed of 11 and 7 arginines, respectively.

In the present invention, A is a drug for prevention or treatment of hair loss and may be, for example, selected from the group consisting of finasteride, dutasteride, minoxidil, episteride, alfatradiol, tofacitinib, and ruxolitinib, with finasteride or dutasteride being preferred.

In the present invention, $L_1$ serves to link the protein transduction domain P to the drug A (when M is a direct bond) or the cleavage site X (when M is a linker represented by Formula 2). In the present invention, the structure of $L_1$ may be represented by Formula 3 or 4,

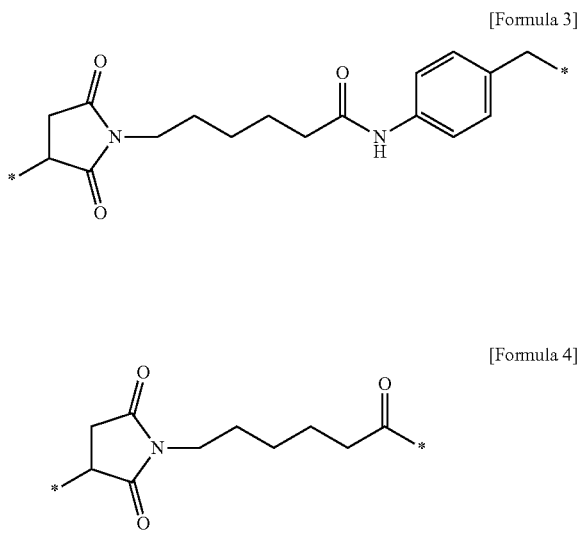

[Formula 3]

[Formula 4]

in Formulas 3 and 4, * is a site where a bond is formed.

In the present invention, the linker $L_1$ may be connected to the C-terminal amino acid residue of the protein transduction domain.

In addition, in the present invention, when the linker $L_1$ is connected to the drug, a carbonyl group of the linker $L_1$ may be connected to an amine group (—$NH_2$), hydroxyl group (—OH), or cyano group (—CN) of the drug for prevention or treatment of hair loss. Preferably, as illustrated in FIG. 1, the carbonyl group of the linker $L_1$ may be connected to the amine group (—$NH_2$) of finasteride, dutasteride, or minoxidil, to the hydroxyl group (—OH) of episteride or alfatradiol, or to the cyano group (—CN) of tofacitinib or ruxolitinib.

In addition, in the present invention, the linker $L_1$ may be connected to the cleavage site X. Here, X refers to an in vivo or target site such as a peptide site that is cleaved in hair papilla cells at a hair loss area, and may be a site recognized by a cytokine, protease, or peptidase. For example, the cleavage site may be a site recognized or cleaved by pro-form of interleukin-1beta (interleukin-1b) that is a cleavage cytokine, caspase (for example, caspase-1, caspase-4, caspase-5), or matrix metalloproteinases (MMPs; for example, MMP1, MMP2, MMP3, MMP7, MMP8, MMP9, MMP10, MMP11, MMP12, MMP13, MMP14, MMP15, MMP16, MMP17, MMP18, MMP19, MM20, PMM21, PMM23A, PMM23B, MMP24, MMP25, MMP26, MMP27, MMP28, and the like), which are present in vivo, in particular, in hair papilla cells. Preferably, the cleavage site may be a site recognized by caspase-1 or interleukin-1b which is highly expressed at a hair loss area, and more preferably may be a peptide (YVAD) represented by SEQ ID NO: 4.

In the present invention, W may be a direct bond or may include at least one amino acid. That is, in the present invention, the protein transduction domain P and the linker $L_1$ may be directly connected to each other, or the protein transduction domain P and the linker $L_1$ may be connected to each other via at least one amino acid interposed therebetween. Here, the amino acid may be selected from 21 amino acids, and may preferably include at least one cysteine.

As an example of the present invention, when at least one cysteine is included between the protein transduction domain P and the linker $L_1$, the thiol group (—SH) of the cysteine may be connected to the linker $L_1$.

In the present invention, M may be a direct bond or a linker represented by Formula 2. That is, in the present invention, the linker $L_1$ may be directly connected to the drug A, or the linker $L_1$ and the drug A may be connected to each other by the linker represented by Formula 2.

In the present invention, when M is the linker represented by Formula 2, the linker $L_2$ in the present invention serves to link the cleavage site X to the drug A. In the present invention, the structure of $L_2$ may be represented by Formula 5,

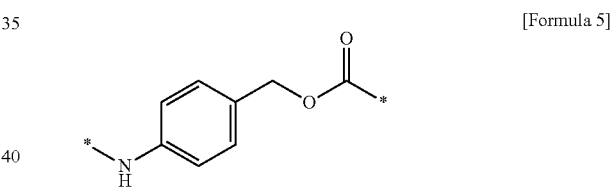

[Formula 5]

in Formula 5, * is a site where a bond is formed.

In the present invention, the linker $L_2$ may be connected to an amine group (—$NH_2$), hydroxyl group (—OH), or cyano group (—CN) of the drug for prevention or treatment of hair loss. The linker $L_2$ may be connected to the amine group (—$NH_2$) of finasteride, dutasteride, or minoxidil, to the hydroxyl group (—OH) of episteride or alfatradiol, or to the amine group (—$NH_2$) of tofacitinib or ruxolitinib.

In the present invention, the compound represented by Formula 1 may be a compound represented by Formula 6 or 7,

[Formula 6]

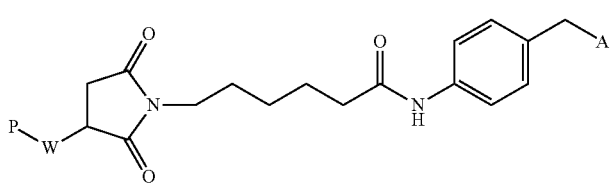

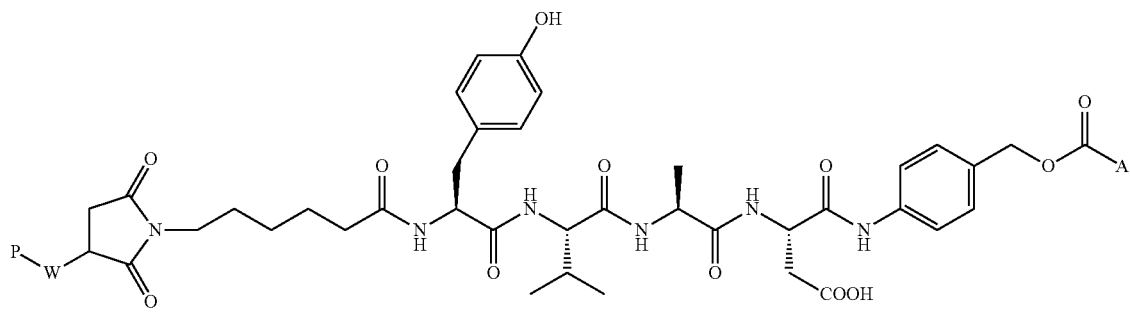

[Formula 7]

in Formulas 6 and 7,

P may be a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP), with CTP (SEQ ID NO: 1), Hph-1 (SEQ ID NO: 2), or Tat (SEQ ID NO: 3) being preferred, W may be a direct bond or at least one amino acid, with at least one cysteine being preferred, and A may be selected from the group consisting of finasteride, dutasteride, minoxidil, episteride, alfatradiol, tofacitinib, and ruxolitinib, with finasteride or dutasteride being preferred.

In the present invention, the compound represented by Formula 1 may be a compound represented by any one of Formulas 8 to 11,

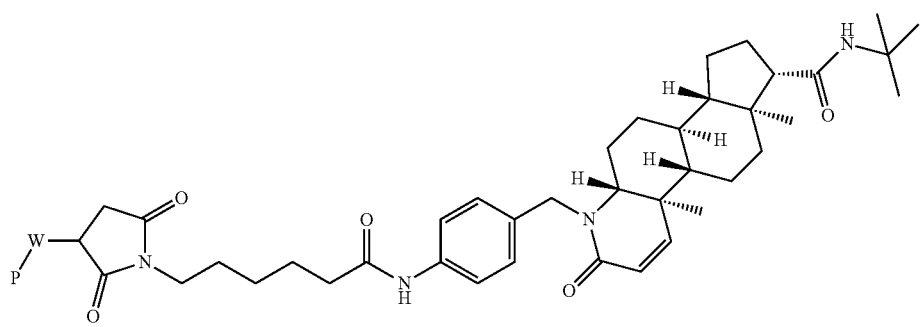

[Formula 8]

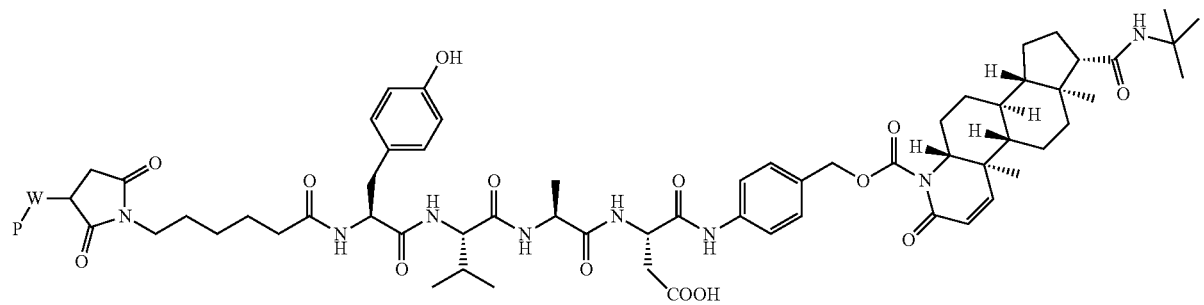

[Formula 9]

[Formula 10]

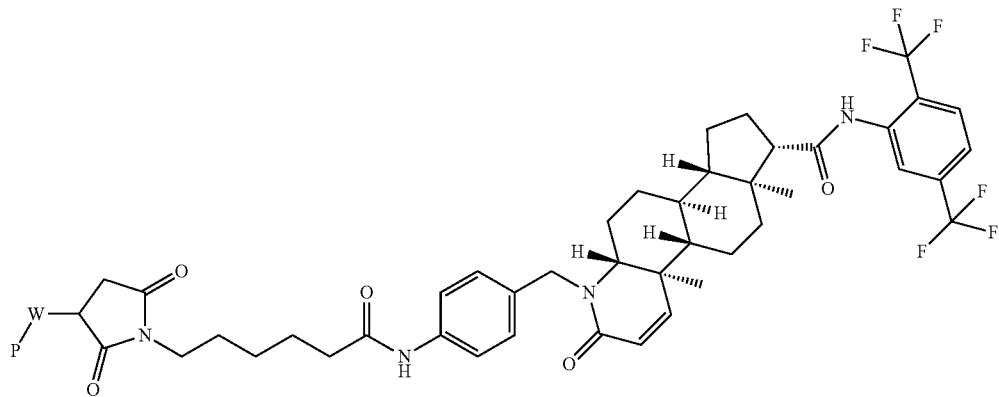

[Formula 11]

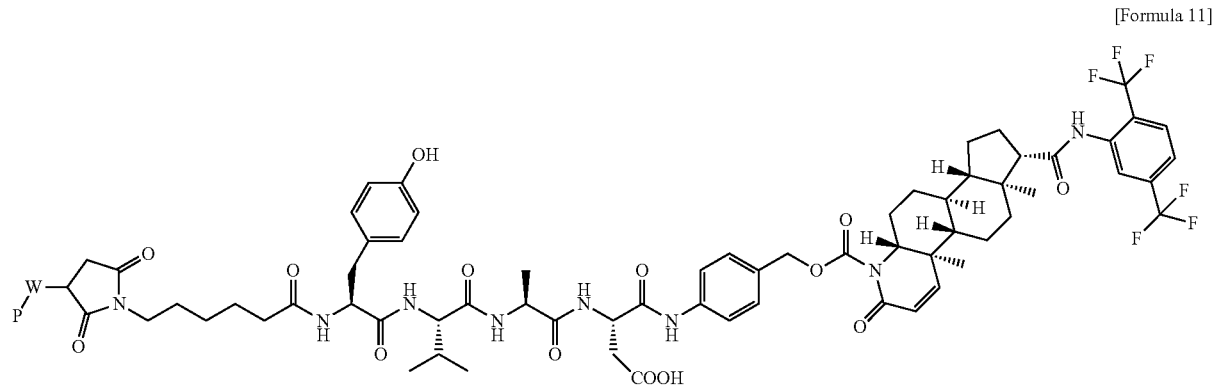

in Formulas 8 to 11,

P may be a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP), with CTP (SEQ ID NO: 1), Hph-1 (SEQ ID NO: 2), or Tat (SEQ ID NO: 3) being preferred, and W may be a direct bond or at least one amino acid, with at least one cysteine being preferred.

In the present invention, the compound represented by Formula 1 may be a compound represented by any one of Formulas 12 to 15,

[Formula 12]

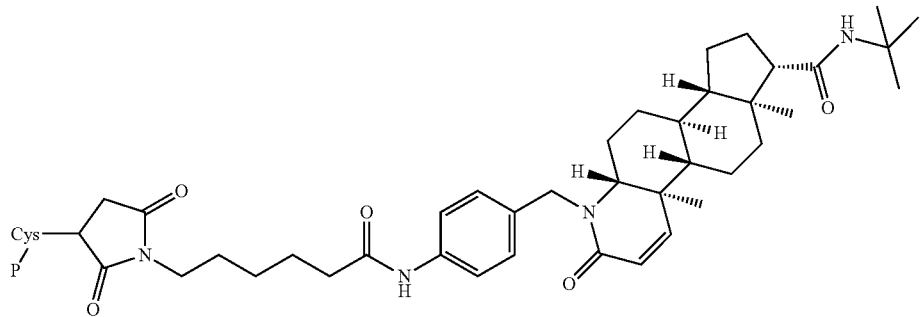

[Formula 13]

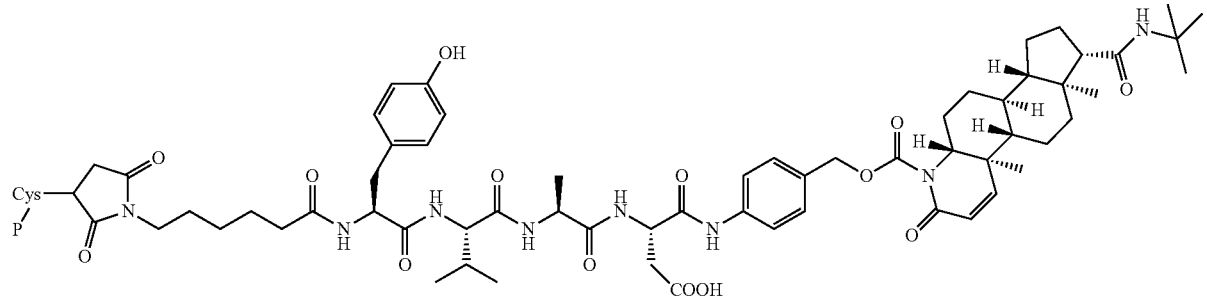

[Formula 14]

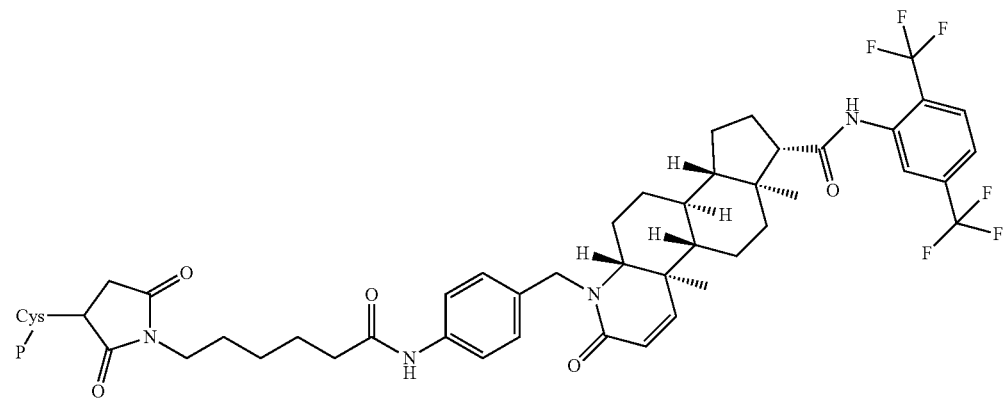

[Formula 15]

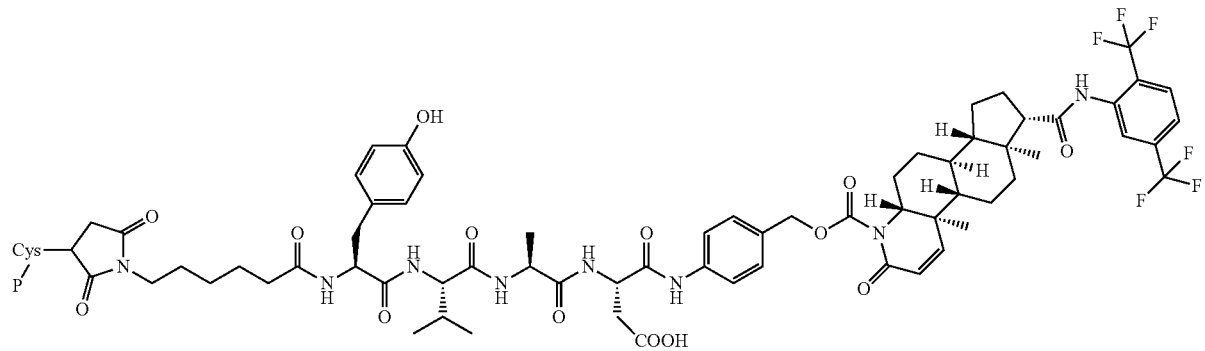

in Formulas 12 to 15,

P is a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP), with CTP (SEQ ID NO: 1), Hph-1 (SEQ ID NO: 2), or Tat (SEQ ID NO: 3) being preferred, and Cys is cysteine.

According to another embodiment of the present invention, there is provided a method for preparing the compound represented by Formula 1, wherein the method may comprise a step of reacting a drug for prevention or treatment of hair loss, 6-maleimidocapronic acid represented by Formula 16, and a protein transduction domain,

[Formula 16]

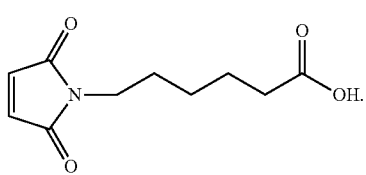

In the present invention, the drug for prevention or treatment of hair loss may be selected from the group consisting of finasteride, dutasteride, minoxidil, episteride, alfatradiol, tofacitinib, and ruxolitinib, with finasteride or dutasteride being preferred.

In the present invention, for the protein transduction domain, any one selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP) may be used, or a macromolecule transduction domain disclosed in WO2016/028036A1 or US Laid-open Patent Application No. 2014-0186379 may be used. However, the present invention is not limited thereto, and any protein transduction domain, which is generally used in the art or commercially available, may be used without limitation. Preferably, the protein transduction domain may be CTP represented by SEQ ID NO: 1, Hph-1 represented by SEQ ID NO: 2, or Tat represented by SEQ ID NO: 3.

In the present invention, before causing the protein transduction domain to be applied to the reaction, a step of additionally extending the C-terminus of the protein transduction domain with at least one amino acid may be performed. Here, the amino acid may be selected from 21 amino acids, and preferably the C-terminus of the protein transduction domain may be additionally extended with at least one cysteine.

In the present invention, the order of reacting the drug for prevention or treatment of hair loss, 6-maleimidocapronic acid represented by Formula 16, and the protein transduction domain is not particularly limited. The drug may be first reacted with 6-M-Aleimidocaproic acid and then the resulting product may be reacted with the protein transduction domain; or the protein transduction domain may be first reacted with 6-maleimidocapronic acid and then the resulting product may be reacted with the drug.

In addition, in the present invention, the reaction may be performed with further addition of a compound represented by Formula 17 and a peptide (YVA) represented by SEQ ID NO: 5,

[Formula 17]

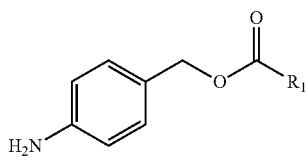

in Formula 17, $R_1$ is a hydroxy group or halogen, wherein the halogen may be fluorine, chlorine, bromine, or iodine, with chlorine being preferred.

In addition, in the present invention, before causing the compound represented by Formula 17 to be applied to the reaction, a step of reacting the compound represented by Formula 17 with a compound represented by Formula 18 may be performed first,

[Formula 18]

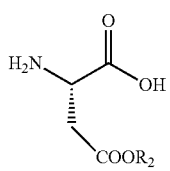

in Formula 18, $R_2$ may be hydrogen or a carboxyl protecting group, wherein the carboxyl protecting group may be, but is not limited to, DMB, Bn, allyl, PfP, Me, PMB, MEM, or t-Bu.

In the present invention, the order of reacting the drug for prevention or treatment of hair loss, the compound represented by Formula 16, the peptide (YVA) represented by SEQ ID NO: 5, the compound represented by Formula 17, the compound represented by Formula 18, and the protein transduction domain is not particularly limited.

As an example, the preparation method of the present invention may comprise steps of:
(1) reacting the compound represented by Formula 17 with the compound represented by Formula 18;
(2) reacting the compound obtained in step (1) with the drug for prevention or treatment of hair loss;
(3) reacting the peptide (YVA) represented by SEQ ID NO: 5 with the compound represented by Formula 16;
(4) reacting the compound obtained in step (2) with the compound obtained in step (3); and
(5) reacting the compound obtained in step (4) with the protein transduction domain.

In the present invention, the order of steps (2) and (3) is not particularly limited. Step (2) may be performed and then step (3) may be performed; step (3) may be performed and then step (2) may be performed; or steps (2) and (3) may be performed at the same time.

In step (1) of the present invention, the compound represented by Formula 17 may be reacted with the compound represented by Formula 18 to prepare a compound represented by Formula 19,

[Formula 19]

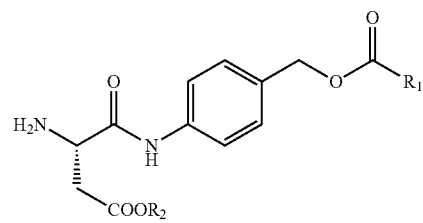

in Formula 19, $R_1$ is a hydroxy group or halogen, wherein the halogen may be fluorine, chlorine, bromine, or iodine, with chlorine being preferred, and $R_2$ is hydrogen or a carboxyl protecting group, wherein the carboxyl protecting group may be, but is not limited to, DMB, Bn, allyl, PfP, Me, PMB, MEM, or t-Bu.

In step (2) of the present invention, the drug for prevention or treatment of hair loss is preferably finasteride or dutasteride.

In the present invention, in step (2), the amine group of finasteride may react with the carboxyl group of the compound represented by Formula 19 prepared in step (1), to form an amide bond.

In the present invention, in step (3), the amine group (—NH₂) of the N-terminus of the peptide (YVA) represented by SEQ ID NO: 5 reacts with the carboxyl group (—COOH) of the compound represented by Formula 16, to form an amide bond.

In the present invention, step (4) may be performed in the presence of a solvent, wherein the solvent used may be, but is not limited to, any one or more selected from the group consisting of hexafluorophosphate benzotriazole tetramethyl uronium (HBTU), N,N-diisopropylethylamine (DIEA), and dimethylformamide (DMF).

In the present invention, in step (4), the amine group (—NH$_2$) of the compound obtained in step (2) reacts with the carboxyl group (—COOH) of the compound obtained in step (3), to form an amide bond.

In the present invention, when R$_2$ in Formula 18 is a carboxyl protecting group, after step (3), an optional step of removing the carboxyl protecting group may be additionally performed. Here, in order to remove the carboxyl protecting group, trifluoroacetic acid (TFA) may be used, and any method used to remove a carboxyl protecting group in the art may be used without limitation.

In the present invention, before performing step (5), the C-terminus of the protein transduction domain may be additionally extended with at least one amino acid. Here, the amino acid may be selected from 21 amino acids, and preferably the C-terminus of the protein transduction domain may be additionally extended with at least one cysteine.

In step (5) of the present invention, the protein transduction domain is preferably CTP (SEQ ID NO: 1), Hph-1 (SEQ ID NO: 2), or Tat (SEQ ID NO: 3).

In the present invention, in step (5), the protein transduction domain may be added at a molar ratio of 0.5 to 5, preferably 1 to 3, with respect to the compound obtained in step (4).

In addition, in the present invention, step (5) may be performed in the presence of a solvent, wherein the solvent used may be, but is not limited to, at least one of dimethyl sulfoxide (DMSO) and N-methylmorpholine (NMM).

In addition, in the present invention, step (5) may be performed at room temperature of 20° C. to 25° C. for 6 to 48 hours, preferably 12 to 24 hours.

However, the preparation method of the present invention is not limited to steps (1) to (5). As another example, the method may comprise reacting the drug with the compound represented by Formula 19, then reacting the resulting product with the polypeptide (YVA) represented by SEQ ID NO: 5, then reacting the resulting product with the compound represented by Formula 16, and then reacting the resulting product with the protein transduction domain. As yet another example, the method may comprise reacting the protein transduction domain with the compound represented by Formula 16, then reacting the resulting product with the peptide (YVA) represented by SEQ ID NO: 5, then reacting the resulting product with the compound represented by Formula 19, and then reacting the resulting product with the drug.

According to yet another embodiment of the present invention, there is provided a composition for prevention, improvement, or treatment of hair loss, comprising, as an active ingredient, the compound represented by Formula 1 of the present invention.

In general, in a case where a drug is conjugated to a protein transduction domain (PTD), activity of the drug is affected due to structural changes or the like. Therefore, substances to be conjugated and specific conjugation sites in the substances to be conjugated are very important. In this regard, for the compound provided by the present invention, a specific drug for prevention or treatment of hair loss and a protein transduction domain are connected to each other via a linker so that structural changes in the drug and the protein transduction domain are minimized, which in turn allows the drug, which is active, to be delivered to a target site. Furthermore, in the present invention, the cleavage site may be further included between the protein transduction domain and the drug. Thus, in a case where the drug is delivered by the protein transduction domain to hair papilla cells at a target hair loss area, the drug is cleaved from the drug delivery vehicle by caspase-1 or pro-form of interleukin-1beta (interleukin-1b) which is hyperactivated at the hair loss area, thereby not only enabling the drug to exhibit activity, but also making it possible to indirectly prevent caspase-1 from converting prointerleukin-1b into IL-1b in the process so that inflammatory responses can be further suppressed.

The composition of the present invention may further comprise another drug for prevention or treatment of hair loss, in addition to the compound represented by Formula 1, in order to increase an effect of preventing, improving, or treating hair loss. Here, as the other drug for prevention or treatment of hair loss, for example, at least one selected from the group consisting of finasteride, dutasteride, minoxidil, episteride, alfatradiol, tofacitinib, and ruxolitinib may be used, and any drug may be included without limitation as long as the drug is another known drug for prevention or treatment of hair loss.

The composition of the present invention may further comprise a known anti-inflammatory agent, in addition to the compound represented by Formula 1, in order to increase an effect of preventing, improving, or treating hair loss. Here, the anti-inflammatory agent includes a steroidal agent such as prednisolone, a non-steroidal agent, or the like; and a pharmaceutically effective amount thereof is known in the art, and a treating physician may adjust the amount in consideration of various conditions such as severity of symptoms and administration combined with chlorogenic acid. In a case where the known anti-inflammatory agent is administered in combination with chlorogenic acid or a derivative thereof in this manner, not only a side effect or the like of the known anti-inflammatory agent may be alleviated by chlorogenic acid or the derivative thereof, but also a synergistic therapeutic effect may be expected. As the case may be, this known anti-inflammatory agent may be administered simultaneously or in the form of a complex preparation with chlorogenic acid of the present invention, or may be administered at a time interval from chlorogenic acid of the present invention.

The composition of the present invention may be used as a pharmaceutical composition, cosmetic composition, or food composition.

According to still yet another embodiment of the present invention, there is provided a method for preventing, improving, or treating hair loss, comprising a step of administering, to a target individual, an effective amount of the composition of the present invention.

In the present invention, the "target individual" refers to an individual who has or is more likely to have hair loss.

In the present invention, the "prevention" may include, without limitation, any act of blocking symptoms of hair loss or suppressing or delaying progression of the symptoms, using the pharmaceutical composition of the present invention.

In the present invention, the "treatment" or "improvement" may include, without limitation, any act of ameliorating or beneficially altering symptoms of hair loss, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

The pharmaceutical composition of the present invention may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a fragrance, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

As used herein, the term "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the present invention in any way. The pharmaceutical composition according to the present invention may be formulated in the form of pills, sugar-coated tablets, capsules, liquids, gels, syrups, slurries, or suspensions.

In the present invention, the cosmetic composition may be prepared in the form of skin softeners, nourishing lotions, nourishing essences, massage creams, cosmetic bath water additives, body lotions, body milks, bath oil, baby oil, baby powders, shower gels, shower creams, sun screen lotions, sun screen creams, suntan creams, skin lotions, skin creams, UV blocking cosmetics, cleansing milks, hair removing agents (for cosmetic purposes), face and body lotions, face and body creams, skin whitening creams, hand lotions, hair lotions, cosmetic creams, Jasmine oil, bath soaps, liquid soaps, cosmetic soaps, shampoos, hand cleaners, medicinal soaps (for non-medical purposes), cream soaps, facial washes, body cleansers, scalp cleansers, hair rinses, toilet soaps, tooth whitening gels, toothpastes, and the like. To this end, the composition of the present invention may further contain either a solvent which is conventionally used for the preparation of cosmetic compositions, or a suitable carrier, excipient, or diluent.

The type of solvent that may further be added to the cosmetic composition of the present invention is not particularly limited, and examples of the solvent may include water, saline, DMSO, or a combination thereof. In addition, examples of the carrier, excipient, or diluent include, but are not limited to, purified water, oil, wax, fatty acids, fatty acid alcohol, fatty acid esters, surfactants, humectants, thickeners, antioxidants, viscosity stabilizers, chelating agents, buffers, lower alcohol, and the like. In addition, the cosmetic composition of the present invention may, if necessary, contain whitening agents, moisturizing agents, vitamins, UV blocking agents, fragrances, dyes, antibiotics, antibacterial agents, and antifungal agents.

Examples of the oil may include hydrogenated vegetable oil, castor oil, cottonseed oil, olive oil, palm kernel oil, jojoba oil, and avocado oil, and examples of the wax may include beeswax, spermaceti, carnauba wax, candelilla wax, montan wax, ceresin wax, liquid paraffin, and lanolin.

Examples of the fatty acids may include stearic acid, linoleic acid, linolenic acid, and oleic acid; examples of the fatty acid alcohol may include cetyl alcohol, octyl dodecanol, oleyl alcohol, panthenol, lanolin alcohol, stearyl alcohol, and hexadecanol; and examples of the fatty acid esters may include isopropyl myristate, isopropyl palmitate, and butyl stearate. Examples of the surfactants may include cationic surfactants, anionic surfactants, and nonionic surfactants, which are known in the art. Among these, if possible, surfactants derived from natural products are preferred.

In addition, the cosmetic composition of the present invention may contain humectants, thickeners, antioxidants, and the like, which are widely known in the cosmetic field, and the types and amounts thereof are as known in the art.

The food composition of the present invention may be prepared in the form of various foods, for example, beverages, gums, tea, vitamin complexes, powders, granules, tablets, capsules, confections, rice cakes, bread, and the like. The food composition of the present invention is composed of a plant extract having little toxicity and side effects, and thus can be used without worries in a case of being ingested for a long time for preventive purposes.

When the miRNA, expression vector, or transformant of the present invention is included in the food composition, it may be added in an amount corresponding to a rate of 0.1% to 50% of the total weight.

Here, in a case where the food composition is prepared in the form of beverages, there is no particular limitation except that the beverage contains the food composition at an indicated proportion, and the beverage may contain various flavoring agents, natural carbohydrates, or the like as additional ingredients, similarly to conventional beverages. That is, examples of the natural carbohydrates may include monosaccharides such as glucose, disaccharides such as fructose, polysaccharides such as sucrose, conventional sugars such as dextrin and cyclodextrin, and sugar alcohol such as xylitol, sorbitol, and erythritol. Examples of the flavoring agents may include natural flavoring agents (thaumatin, stevia extracts (such as rebaudioside A), glycyrrhizin, and the like) and synthetic flavoring agents (saccharin, aspartame, and the like).

In addition, the food composition of the present invention may contain various nutrients, vitamins, minerals (electrolytes), flavorings such as synthetic flavorings and natural flavorings, colorants, pectic acid and salts thereof, alginic acid and salts thereof, organic acids, protective colloidal thickeners, pH adjusting agents, stabilizers, preservatives, glycerin, alcohol, carbonizing agents used in carbonated beverages, and the like.

These ingredients may be used individually or in combination. A proportion of such additives is not so important, and is generally selected from the range of 0.1 to about 50 parts by weight per 100 parts by weight of the composition of the present invention.

Advantageous Effects of Invention

The composition provided by the present invention is delivered to the skin, in particular, the composition is effectively delivered into hair papilla cells in a hair loss area, which is a target area, wherein a cytokine or enzyme highly expressed in the hair loss area causes a drug to be separated from a compound contained in the composition so that the drug effectively exhibits activity, which can ultimately promote hair growth and/or hair regrowth.

DETAILED DESCRIPTION OF INVENTION

Figure 1:
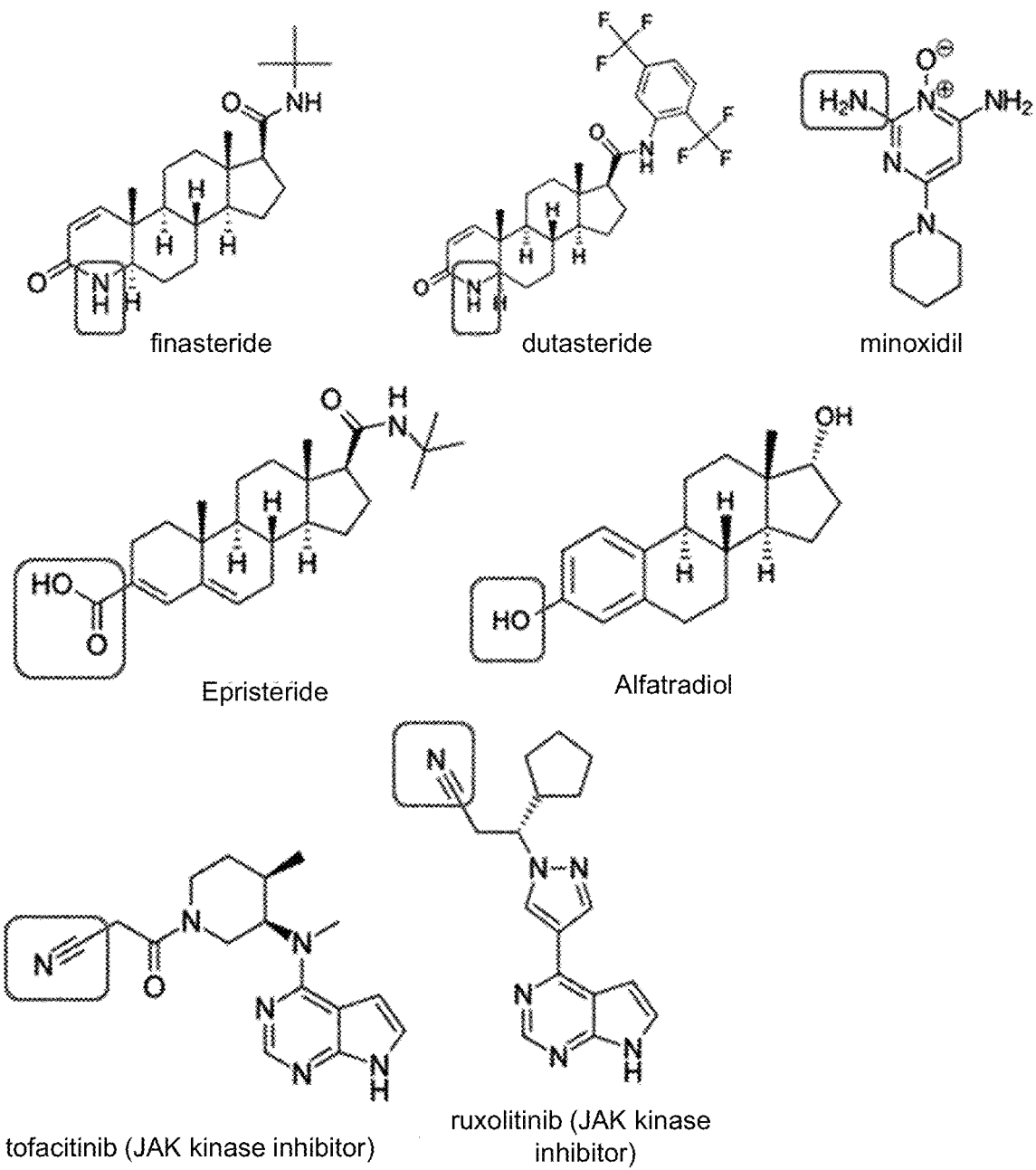
FIG. 1 illustrates exemplary structures of drugs for prevention or treatment of hair loss which may be used in the compound of the present invention, in which functional groups that can be connected to a linker ($L_1$ or $L_2$) are shown.

The present invention relates to a pharmaceutical composition for prevention or treatment of hair loss, comprising, as an active ingredient, the compound represented by Formula 6 or 7,

[Formula 6]

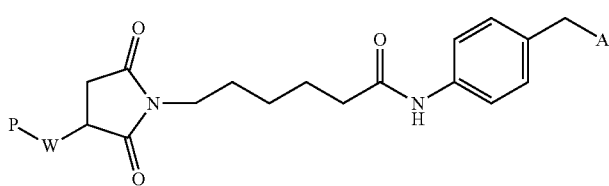

[Formula 7]

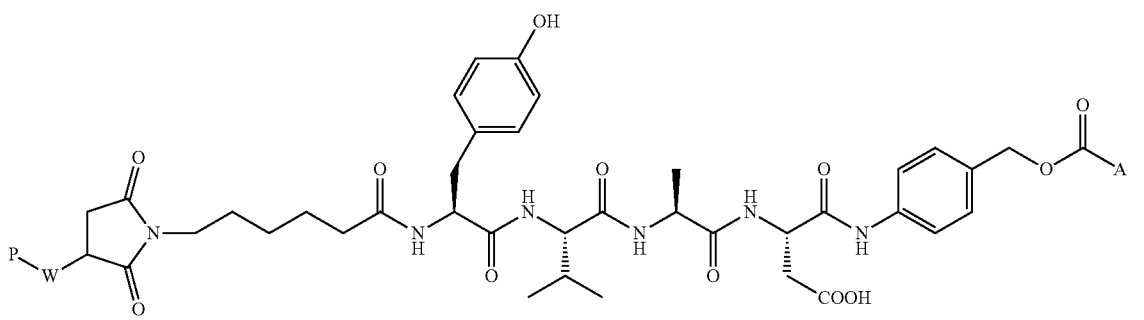

in Formulas 6 and 7,

P may be a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP), with CTP (SEQ ID NO: 1), Hph-1 (SEQ ID NO: 2), or Tat (SEQ ID NO: 3) being preferred, W may be a direct bond or at least one amino acid, with at least one cysteine being preferred, and A may be selected from the group consisting of finasteride, dutasteride, minoxidil, episteride, alfatradiol, tofacitinib, and ruxolitinib, with finasteride or dutasteride being preferred.

Hereinafter, the present invention will be described in more detail by way of examples. These examples are merely given to illustrate the present invention in more detail, and it will be apparent to those skilled in the art that according to the gist of the present invention, the scope of the present invention is not limited by these examples.

EXAMPLES

[Preparation Example 1]

As protein transduction domains, CTP represented by SEQ ID NO: 1, Hph-1 represented by SEQ ID NO: 2, and Tat represented by SEQ ID NO: 3 were prepared, and then the respective C-termini thereof were additionally extended with the amino acid cysteine to prepare peptides represented by SEQ ID NOs: 6, 7, and 8, respectively.

[Example 1] Preparation of CTP-fina

The compound represented by Formula A1 containing finasteride was mixed in a 1:1 molar ratio with the peptide (CTP+cysteine) represented by SEQ ID NO: 6 prepared in Preparation Example 1, in the presence of DMSO and NMM, and then reaction was allowed to proceed at room temperature for 12 hours, to prepare a final compound represented by Formula E1. In Formula E1, '-Cys-S—' refers to a structure in which a thiol group contained in cysteine (Cys) is connected to pyrrolidine-2,5-dione.

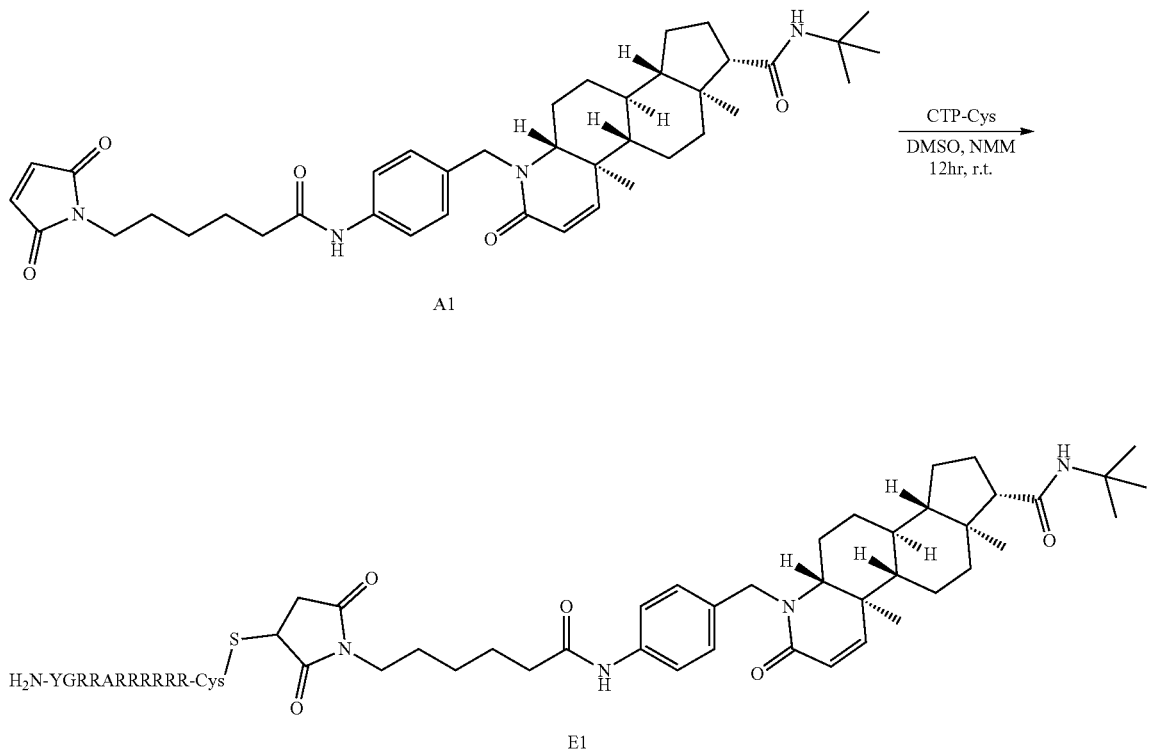

<Scheme 1>

[Example 2] Preparation of CTP-duta

The compound represented by Formula A2 containing dutasteride was mixed in a 1:1 molar ratio with the peptide (CTP+cysteine) represented by SEQ ID NO: 6 prepared in Preparation Example 1, in the presence of DMSO and NMM, and then reaction was allowed to proceed at room temperature for 12 hours, to prepare a final compound represented by Formula E2. In Formula E2, '-Cys-S—' refers to a structure in which a thiol group contained in cysteine (Cys) is connected to pyrrolidine-2,5-dione.

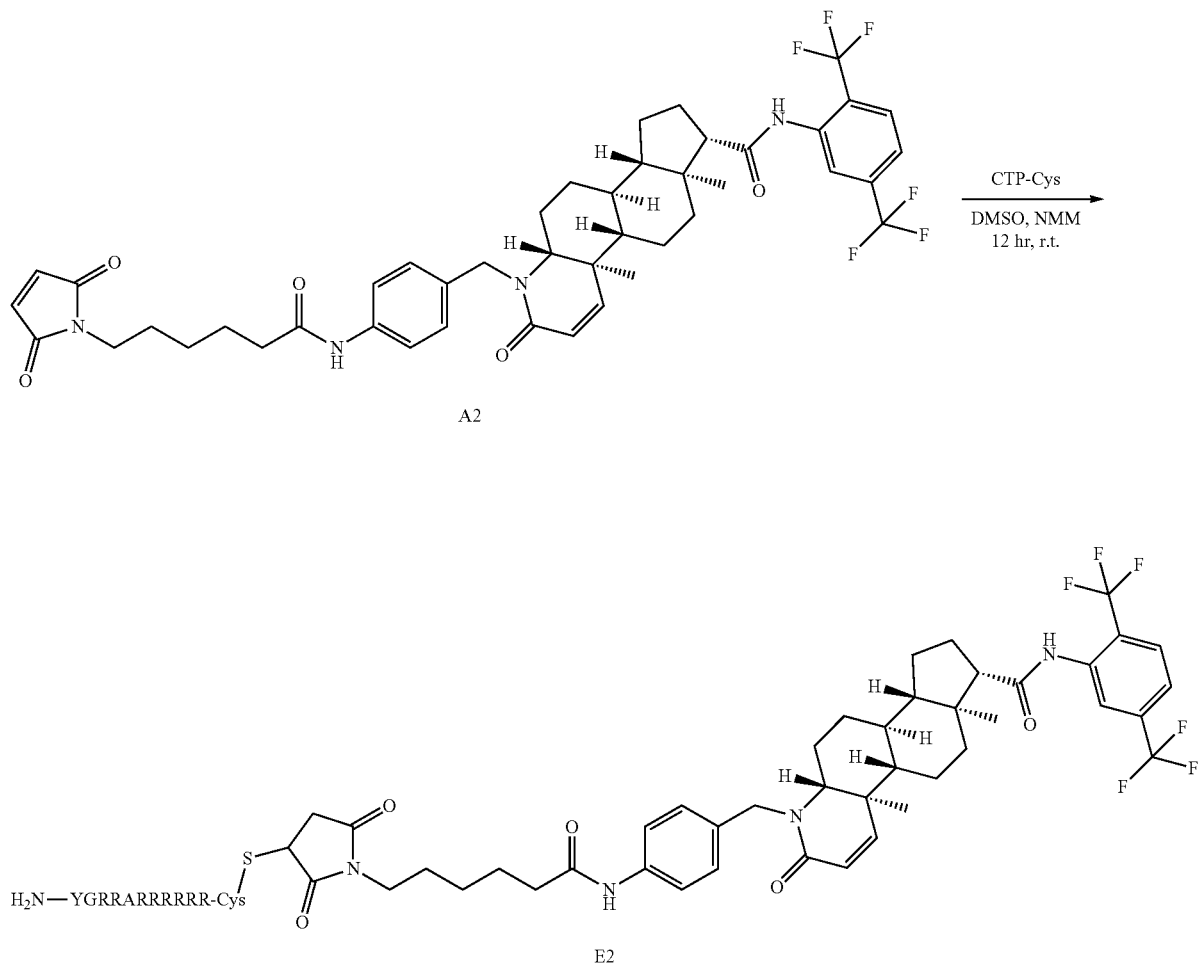

[Example 3] Preparation of hph-1-fina

A compound represented by Formula E3 was prepared in the same method as in Example 1, except that in Example 1, the peptide (Hph-1+cysteine) represented by SEQ ID NO: 7 was used in place of the peptide represented by SEQ ID NO: 6 used as the protein transduction domain. In Formula E3, '-Cys-S—' refers to a structure in which a thiol group contained in cysteine (Cys) is connected to pyrrolidine-2,5-dione.

[Example 4] Preparation of hph-1-duta

A compound represented by Formula E4 was prepared in the same method as in Example 1, except that in Example 2, the peptide (Hph-1+cysteine) represented by SEQ ID NO: 7 was used in place of the peptide represented by SEQ ID NO: 6 used as the protein transduction domain. In Formula E4, '-Cys-S—' refers to a structure in which a thiol group contained in cysteine (Cys) is connected to pyrrolidine-2,5-dione.

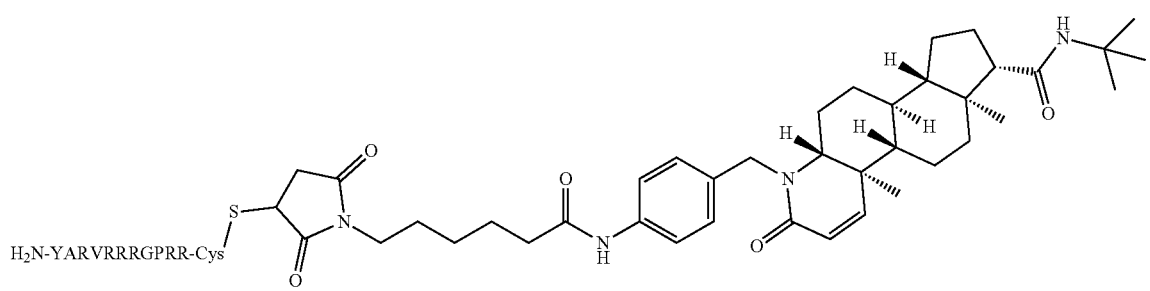

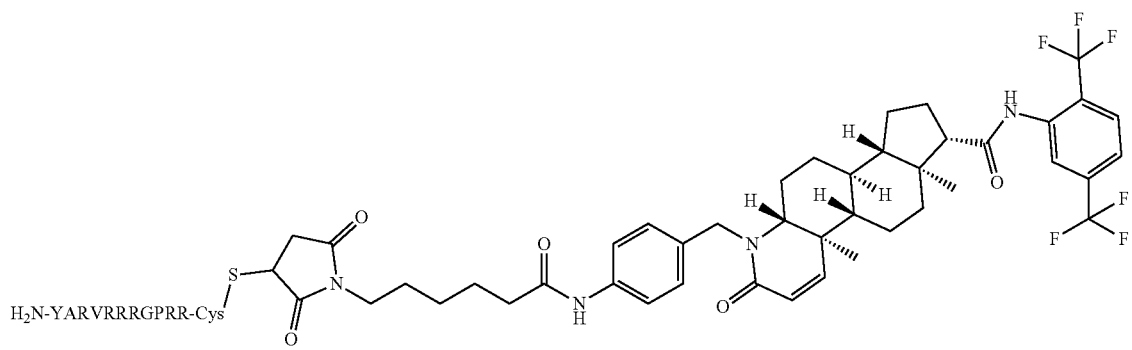

E4

[Example 5] Preparation of Tat-fina

A compound represented by Formula E5 was prepared in the same method as in Example 1, except that in Example 2, the peptide (Tat+cysteine) represented by SEQ ID NO: 8 was used in place of the peptide represented by SEQ ID NO: 6 used as the protein transduction domain. In Formula E5, '-Cys-S—' refers to a structure in which a thiol group contained in cysteine (Cys) is connected to pyrrolidine-2,5-dione.

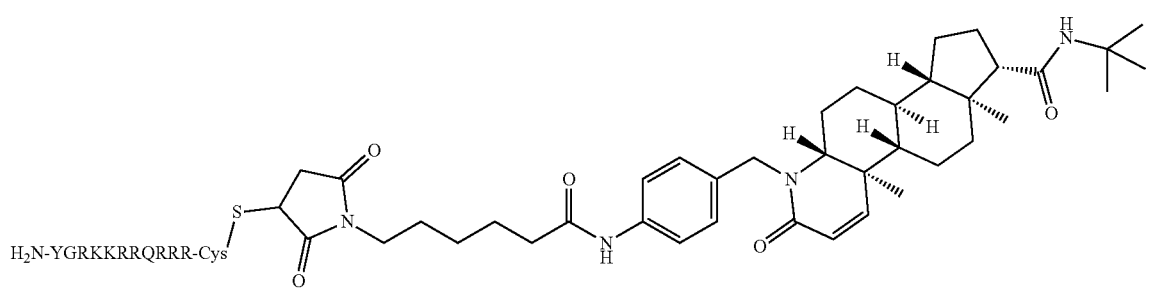

E5

[Example 6] Preparation of Tat-duta

A compound represented by Formula E6 was prepared in the same method as in Example 1, except that in Example 2, the peptide (Tat+cysteine) represented by SEQ ID NO: 8 was used in place of the peptide represented by SEQ ID NO: 6 used as the protein transduction domain. In Formula E6, '-Cys-S—' refers to a structure in which a thiol group contained in cysteine (Cys) is connected to pyrrolidine-2,5-dione.

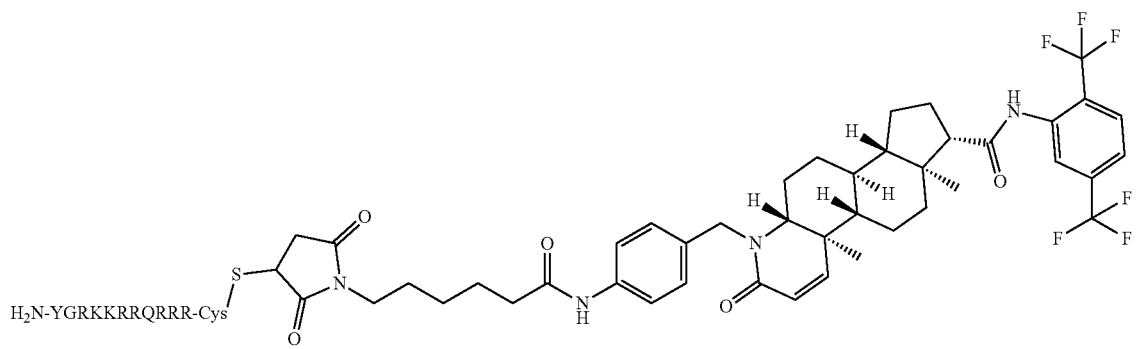

E6

[Preparation Example 2]

(S)-2-amino-4-(tert-butoxy)-4-oxobutanoic acid represented by Formula X1 was reacted with 4-aminobenzyl carbonochloridate represented by Formula X2, to prepare a compound represented by Formula B1.

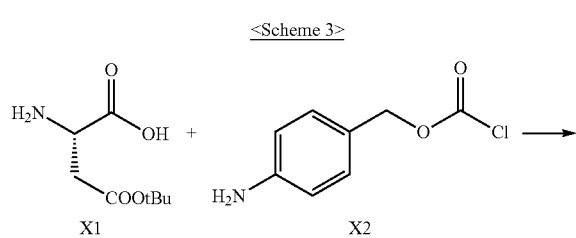

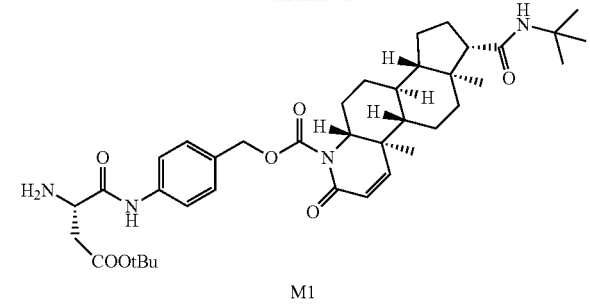

[Preparation Example 3]

The compound represented by Formula B1 was reacted with finasteride represented by Formula X3 in the presence of NaH, to prepare an intermediate compound represented by Formula M1.

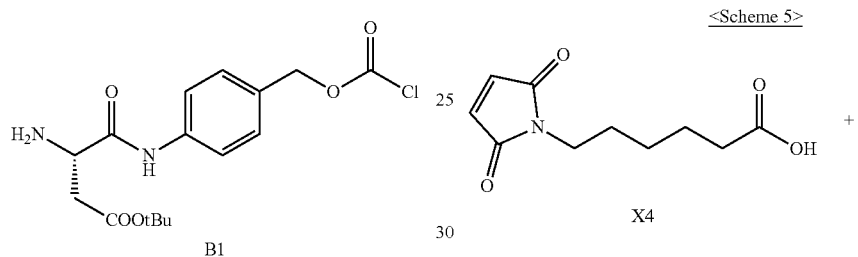

[Preparation Example 4]

6-Maleimidocapronic acid represented by Formula X4 was reacted with a compound represented by Formula X5 (peptide represented by SEQ ID NO: 5), to prepare an intermediate compound represented by Formula M2.

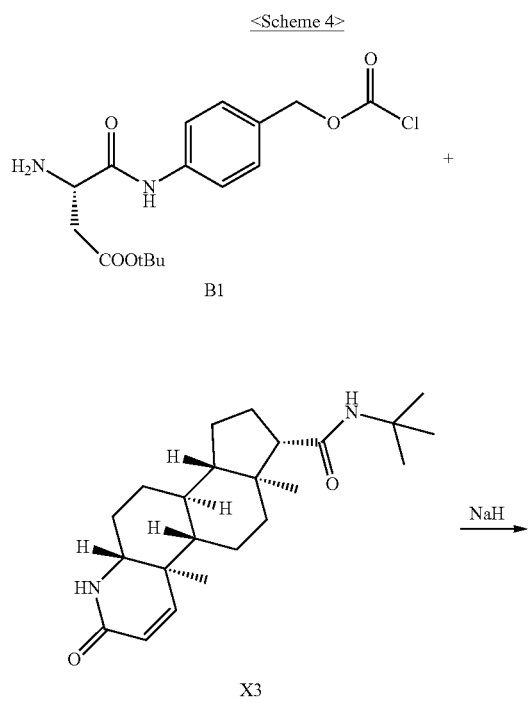

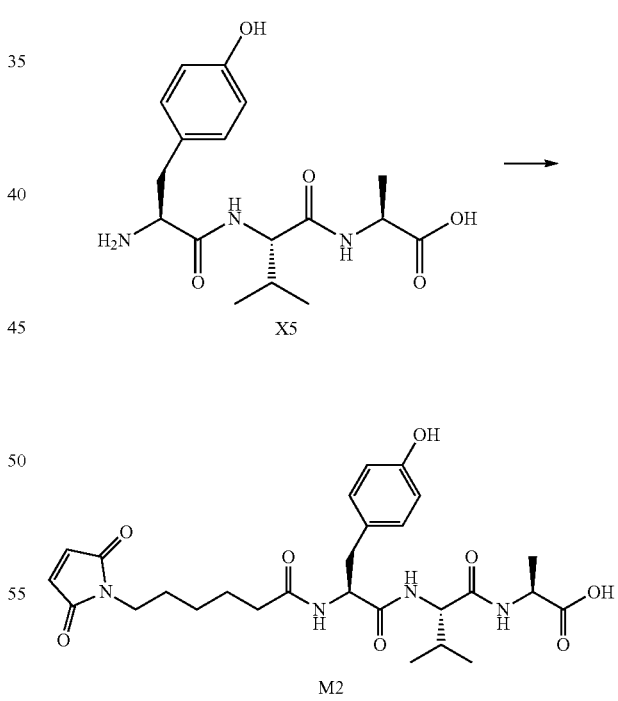

[Example 7] Preparation of CTP-cas1-fina

1. Step 1

As shown in Scheme 6, the intermediate compound represented by Formula M1 was reacted with the intermediate compound represented by Formula M2 in the presence of HBTU, DIEA, and DMF, to prepare a compound represented by Formula A3.

<Scheme 6>
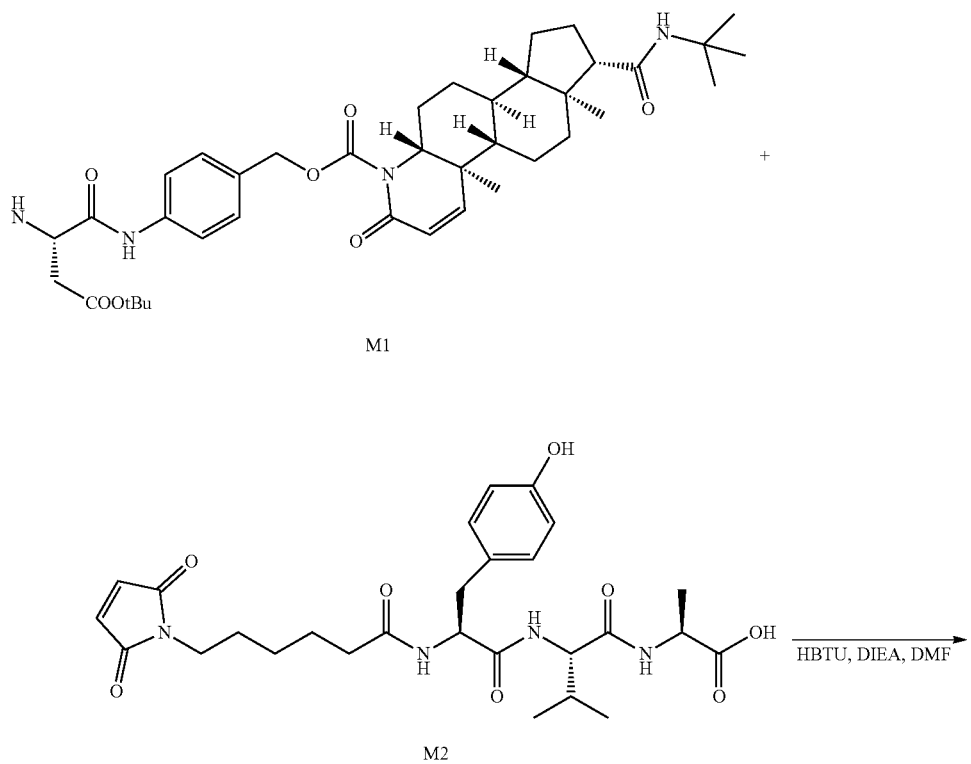
M1
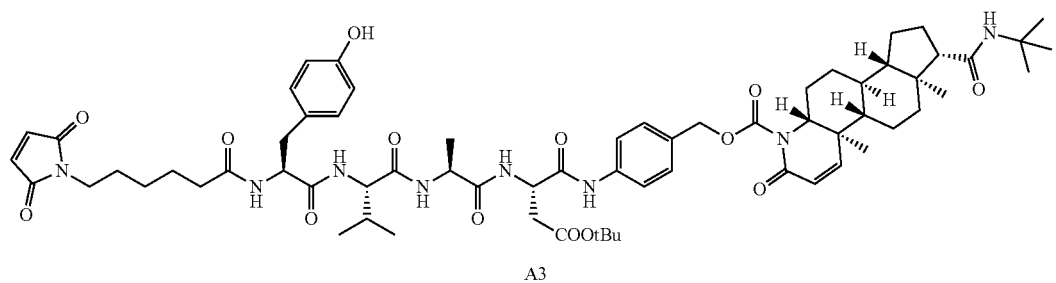
M2
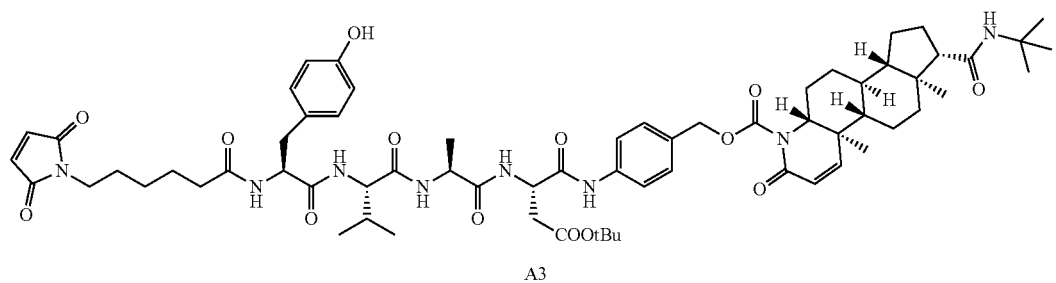
A3
2. Step 2
The compound represented by Formula A3 obtained in Step 1 was allowed to react under 30% TFA so that the tert-butyl group, which is a carboxyl protecting group, is removed, thereby obtaining a compound represented by Formula A4.
<Scheme 7>
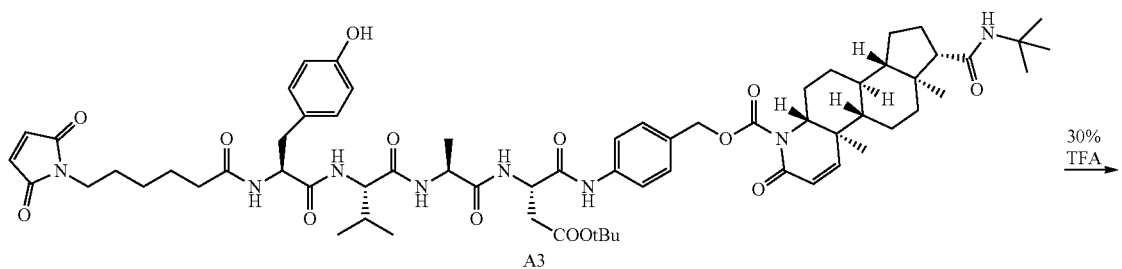
A3

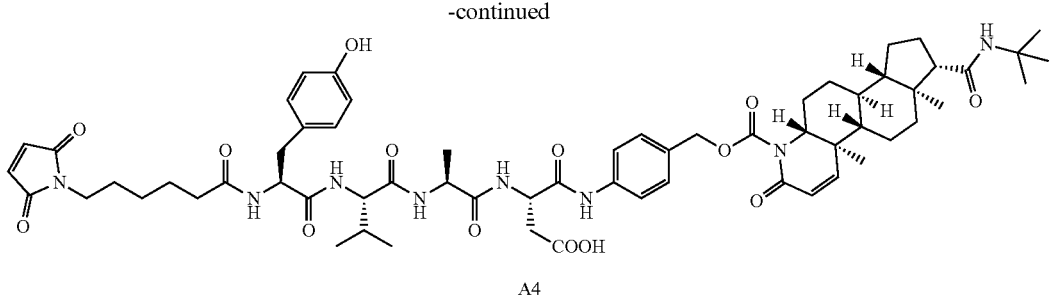

A4

3. Step 3

As shown in Scheme 8, the compound represented by Formula A4 obtained in Step 2, was mixed in a 1:1 molar ratio with the peptide represented by SEQ ID NO: 6 obtained in Preparation Example 1, in the presence of DMSO and NMM, and then reaction was allowed to proceed at room temperature for 12 hours, to prepare a final compound represented by Formula E7. In Formula E7, '-Cys-S—' refers to a structure in which a thiol group contained in cysteine (Cys) is connected to pyrrolidine-2,5-dione.

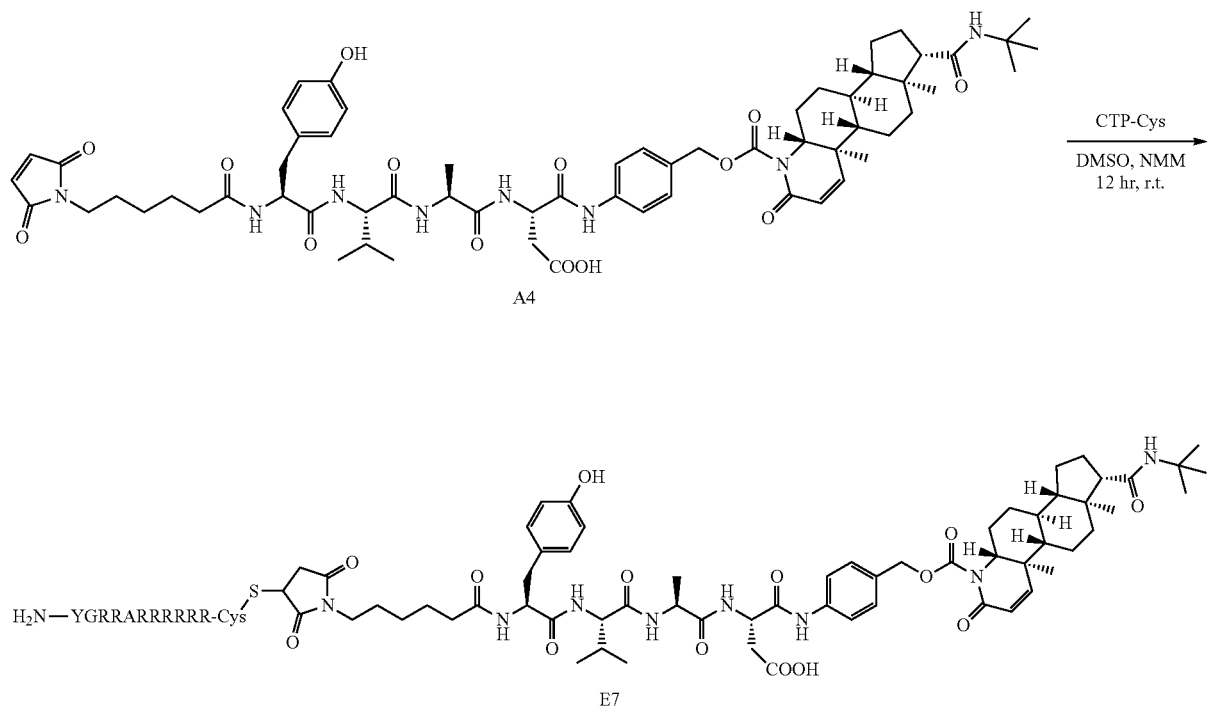

<Scheme 8>

[Preparation Example 5]

The compound represented by Formula B1 was reacted with dutasteride represented by Formula X4 in the presence of NaH, to prepare an intermediate compound represented by Formula M3.

<Scheme 9>

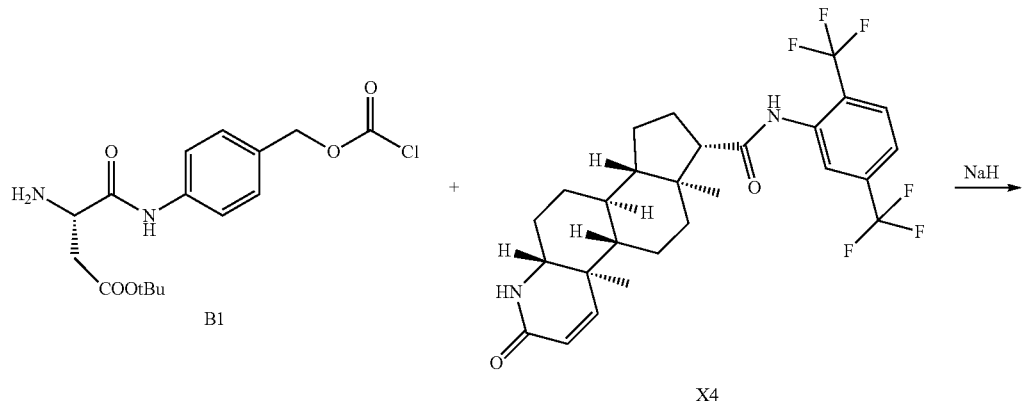

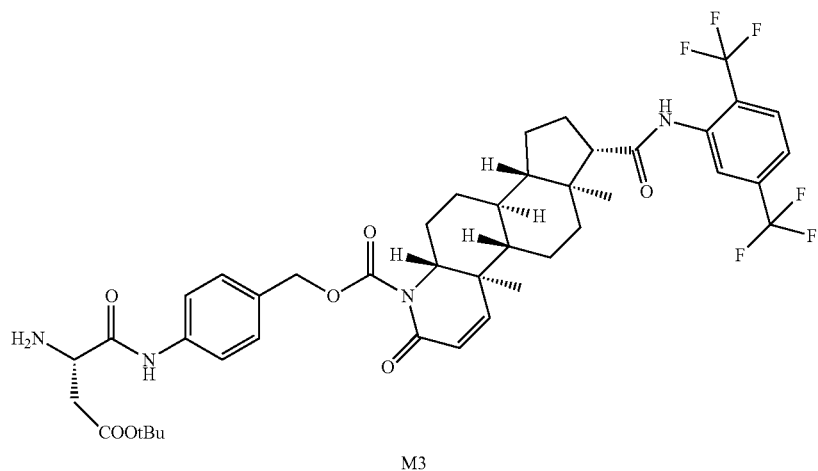

[Example 8] Preparation of CTP-cas1-duta

A final compound represented by Formula E8 was prepared in the same method as in Example 7, except that in Example 7, the compound represented by Formula M3 obtained in Preparation Example 5 was used in place of the compound represented by Formula M1. In Formula E8, '-Cys-S—' refers to a structure in which a thiol group contained in cysteine (Cys) is connected to pyrrolidine-2,5-dione.

[Example 9] Preparation of hph-1-cas1-fina

A compound represented by Formula E9 was prepared in the same method as in Example 7, except that in Step 3 of Example 7, the peptide (Hph-1+cysteine) represented by SEQ ID NO: 7 was used in place of the peptide represented by SEQ ID NO: 6 used as the protein transduction domain. In Formula E9, '-Cys-S—' refers to a structure in which a thiol group contained in cysteine (Cys) is connected to pyrrolidine-2,5-dione.

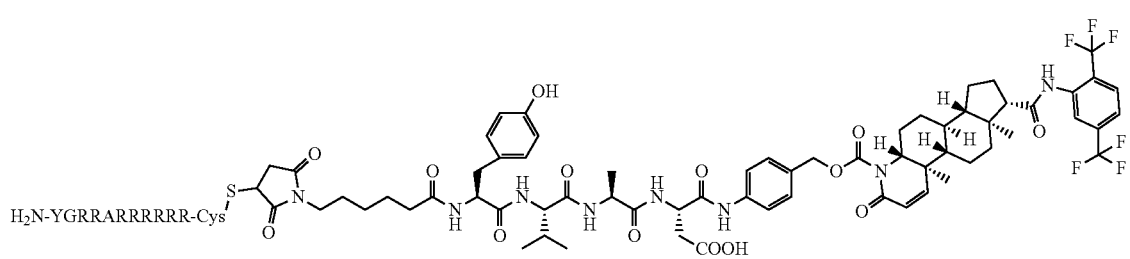

E8

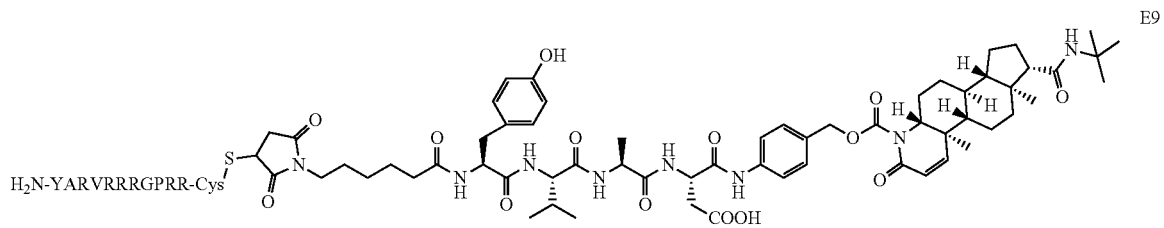

E9

[Example 10] Preparation of hph-1-cas1-duta

A compound represented by Formula E10 was prepared in the same method as in Example 8, except that in Example 8, the peptide (Hph-1+cysteine) represented by SEQ ID NO: 7 was used in place of the peptide represented by SEQ ID NO: 6 used as the protein transduction domain. In Formula E10, '-Cys-S—' refers to a structure in which a thiol group contained in cysteine (Cys) is connected to pyrrolidine-2,5-dione.

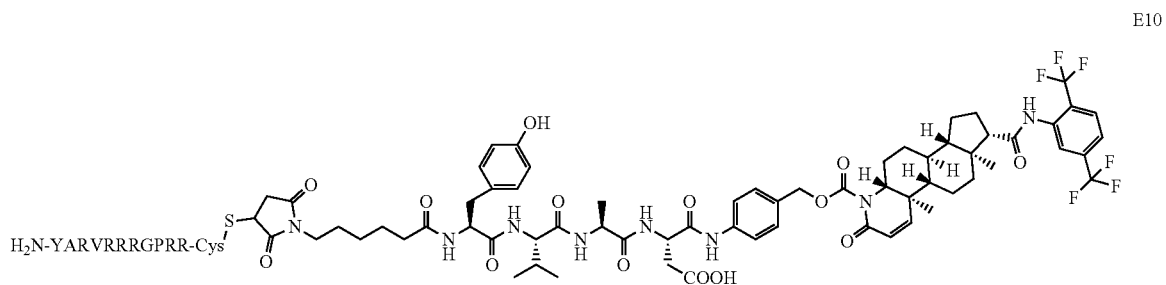

E10

[Example 11] Preparation of Tat-cas1-fina

A compound represented by Formula E11 was prepared in the same method as in Example 7, except that in Step 3 of Example 7, the peptide (Tat+cysteine) represented by SEQ ID NO: 8 was used in place of the peptide represented by SEQ ID NO: 6 used as the protein transduction domain. In Formula E11, '-Cys-S—' refers to a structure in which a thiol group contained in cysteine (Cys) is connected to pyrrolidine-2,5-dione.

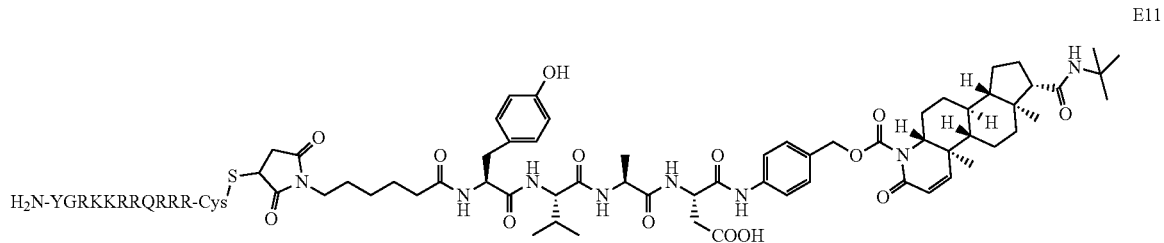

E11

[Example 12] Preparation of Tat-cas1-duta

A compound represented by Formula E12 was prepared in the same method as in Example 8, except that in Example 8, the peptide (Tat+cysteine) represented by SEQ ID NO: 8 was used in place of the peptide represented by SEQ ID NO: 6 used as the protein transduction domain. In Formula E12, '-Cys-S—' refers to a structure in which a thiol group contained in cysteine (Cys) is connected to pyrrolidine-2,5-dione.

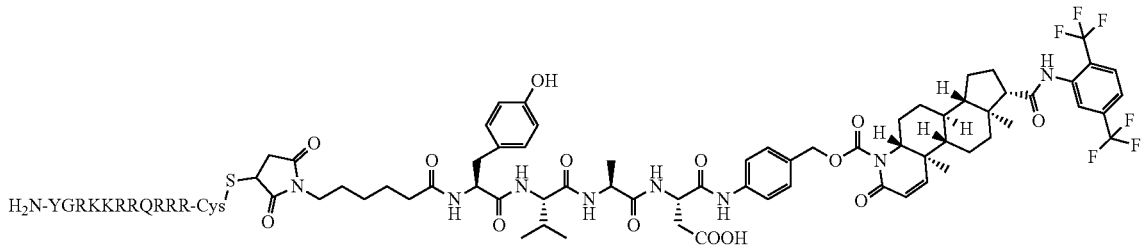

[Experimental Example 1] Identification by HPLC

Compound E1 obtained in Example 1, Compound E7 obtained in Example 7, and finasteride were prepared. Then, these compounds were treated with caspase-1, and analyzed with high performance liquid chromatography (HPLC). The results are illustrated in FIGS. 2 and 3.

Figure 2:
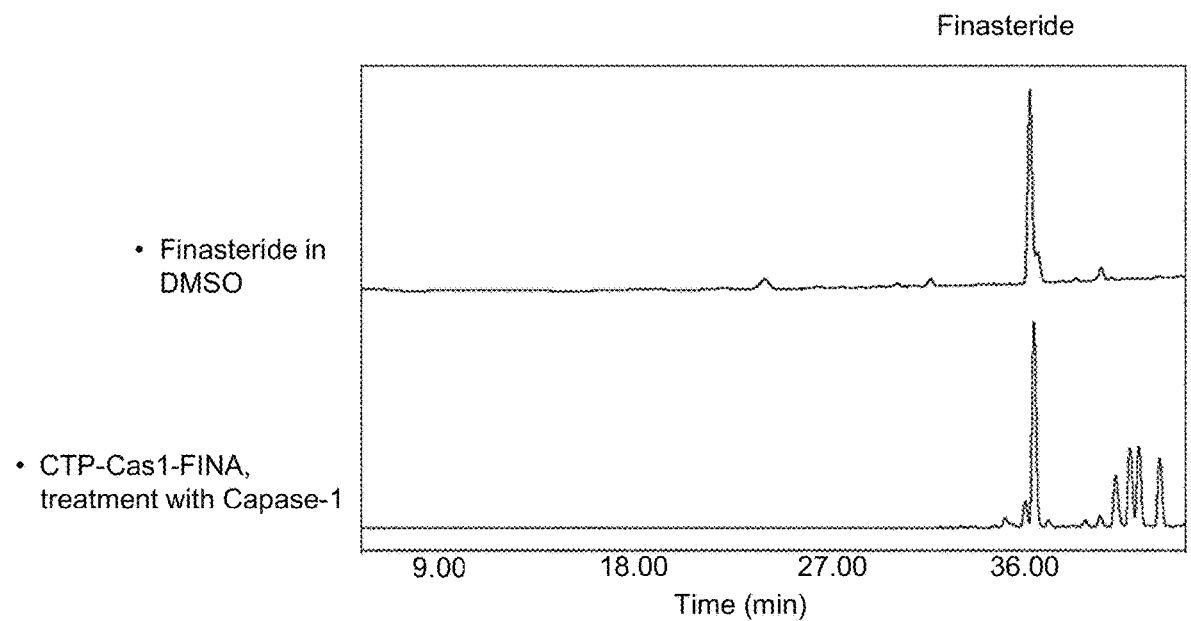
FIG. 2 illustrates results obtained by subjecting finasteride and Compound E7 (CTP-Cas1-FINA) obtained in Example 7 to treatment with caspase-1 and then performing HPLC analysis, in Experimental Example 1.
Figure 3:
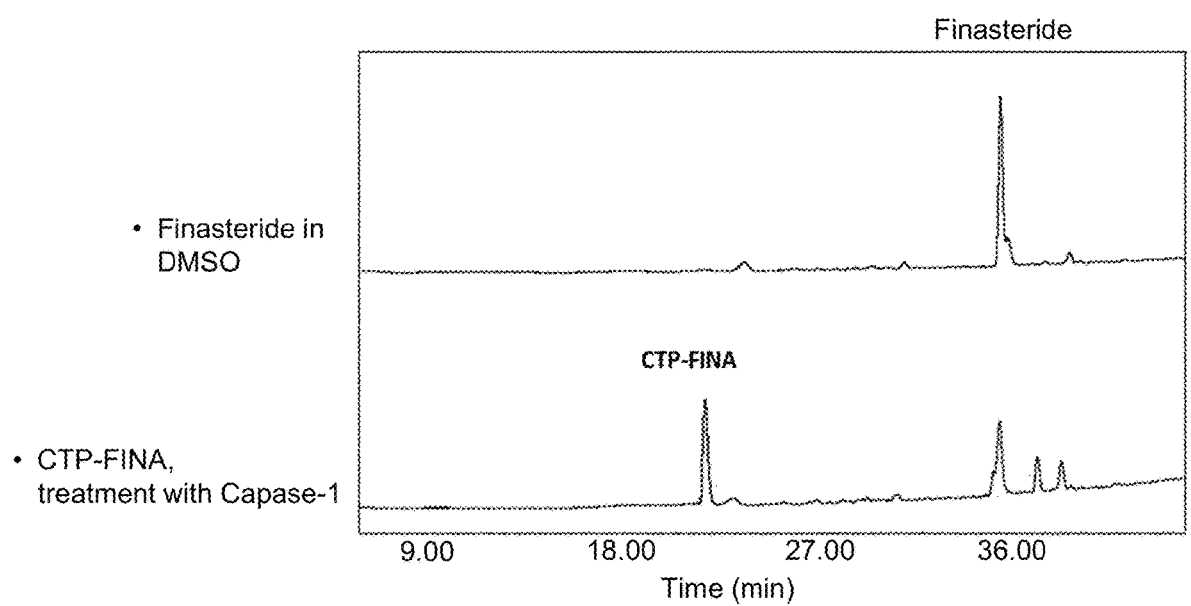
FIG. 3 illustrates results obtained by subjecting finasteride and Compound E1 (CTP-FINA) obtained in Example 1 to treatment with caspase-1 and then performing HPLC analysis, in Experimental Example 1.

As illustrated in FIGS. 2 and 3, from the HPLC analysis results, it was possible to identify the compound of the present invention. In particular, as illustrated in FIG. 2, it was found that when Compound E7 having a cleavage site is treated with caspase-1, the compound is cleaved into two moieties, that is, finasteride and the protein transduction domain.

[Experimental Example 2] Identification of Therapeutic Effect on Hair Loss

In order to test a therapeutic effect, on hair loss, of the compound according to the present invention, inhibitory capacity thereof on the enzyme 5-alpha reductase, known to induce hair loss, was checked.

Figure 4:
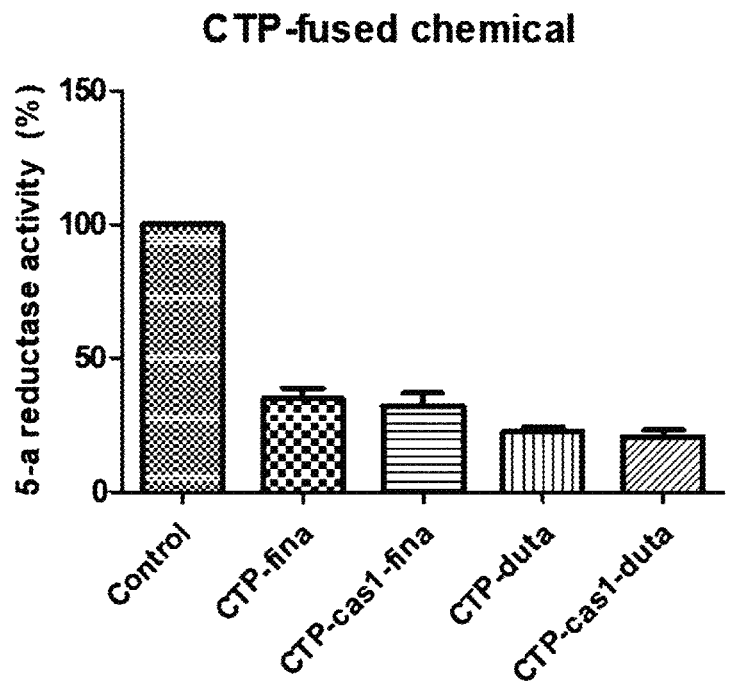
FIG. 4 illustrates results obtained by identifying inhibitory capacity, on the enzyme 5-alpha reductase, of the compounds prepared according to Examples 1, 2, 7, and 8, in Experimental Example 2.
Figure 5:
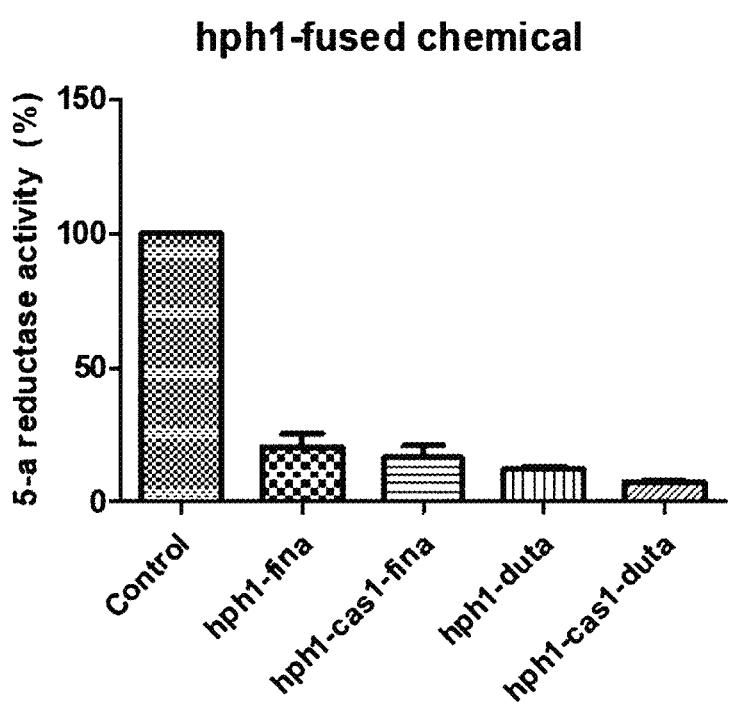
FIG. 5 illustrates results obtained by identifying inhibitory capacity, on the enzyme 5-alpha reductase, of the compounds prepared according to Examples 3, 4, 9, and 10, in Experimental Example 2.
Figure 6:
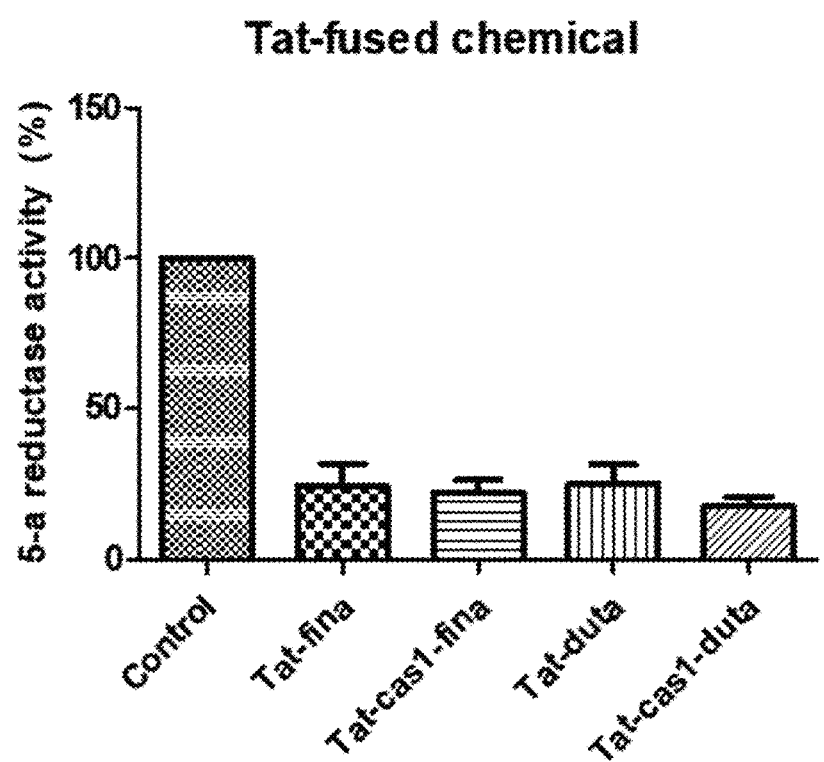
FIG. 6 illustrates results obtained by identifying inhibitory capacity, on the enzyme 5-alpha reductase, of the compounds prepared according to Examples 5, 6, 11, and 12, in Experimental Example 2.

Specifically, cultured LNCaP cells (androgen receptor positive-human cancer cell line) were trypsinized with trypsin and centrifuged at 1500 rpm for 2 minutes to recover the cells. Washing with PBS was performed three times, and then the cells were evenly mixed with a pipette. Subsequently, ultrasonication was performed three times at 4° C. (on ice). Thereafter, centrifugation was performed at 4° C. for 15 minutes at 3000 rpm, to remove cell debris. The supernatant was used as the enzyme 5-alpha reductase. 50 uL of each sample was placed in 96 wells for ELISA kit. The compounds prepared in Examples 1 to 12 were added thereto and incubation was performed at room temperature for 30 minutes. Treatment with 100 uL of conjugate or 2 nM testosterone provided by CUSABIO's 5-alpha reductase ELISA kit was performed, and then incubation was performed at 37° C. for 1 hour. Washing with a washing solution was performed five times in total, and 50 uL of Substrate A and 50 uL of Substrate B, provided by the ELISA kit, were added thereto. Then, wrapping in silver foil was performed and incubation was performed at room temperature for 15 minutes. Then, 50 uL of stop solution was added and mixing was performed. Thereafter, the optical density (O.D.) thereof was measured at a wavelength of 450 nm with a microplate reader, and the results are illustrated in FIGS. 4 to 6. FIG. 4 illustrates the results for the compounds (Examples 1, 2, 7, and 8) obtained using CTP as the protein transduction domain; FIG. 5 illustrates the results for the compounds (Examples 3, 4, 9, and 10) obtained using Hph-1 as the protein transduction domain; and FIG. 6 illustrates the results for the compounds (Examples 5, 6, 11, and 12) obtained using Tat as the protein transduction domain.

As illustrated in FIGS. 4 to 6, it was found that activity of the enzyme 5-alpha reductase, which is known to induce hair loss, is effectively inhibited in a case of being treated with the compound according to the present invention. In particular, it was found that the compound having a cleavage site included between the protein transduction domain and the drug has superior inhibitory capacity on the enzyme 5-alpha reductase as compared with the compound not having the cleavage site.

The compound synthesized in the present invention has superior skin and cell permeability as compared with a case where the drug for treatment of hair loss is administered with the protein transduction domain. The compound of the present invention allows the drug to be effectively delivered even to cells in the dermal layer. Moreover, in a case where the compound is delivered to a target tissue, the cleavage site therein is cleaved by interleukin-1b, caspase that is an enzyme, or the like which is highly expressed at a hair loss area, so that the drug can effectively exhibit activity.

As stated above, specific parts of the present invention have been described in detail. However, it is apparent to those skilled in the art that such specific description is only for illustrating preferred embodiments, and the scope of the present invention is not limited thereto. Accordingly, the substantial scope of the present invention will be defined by the appended claims and equivalents thereof.

INDUSTRIAL APPLICABILITY

The present invention relates to a method for effectively preventing or treating hair loss.

```
Sequence List Free Text
CTP sequence
SEQ ID NO: 1:
YGRRARRRRRR

Hph-1 sequence
SEQ ID NO: 2:
YARVRRRGPRR

Tat sequence
SEQ ID NO: 3:
YGRKKRRQRRR

Cleavage site
SEQ ID NO: 4:
YVAD

SEQ ID NO: 5
YVA

CTP sequence + cysteine extension
SEQ ID NO: 6:
YGRRARRRRRRC

Hph-1 sequence + cysteine extension
SEQ ID NO: 7:
YARVRRRGPRRC

Tat sequence + cysteine extension
SEQ ID NO: 8:
YGRKKRRQRRRC
```

The invention claimed is:

1. A method for preventing or treating hair loss, comprising administering, to a target individual, an effective amount of a compound represented by Formula 1:

$$P\text{-}W\text{-}L_1\text{-}M\text{-}A \qquad \text{[Formula 1]}$$

in which

P is a protein transduction domain (PTD);

W is a direct bond or includes at least one amino acid;

$L_1$ is a linker, wherein $L_1$ is represented by Formula 3 or Formula 4,

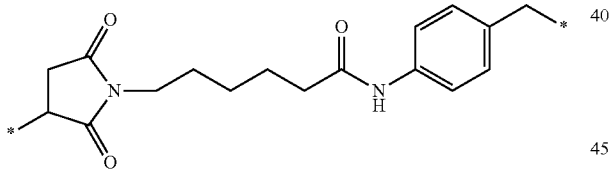

[Formula 3]

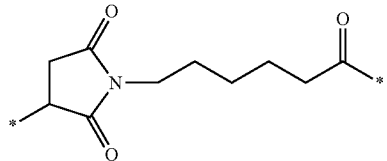

[Formula 4]

in which Formulas 3 and 4, * is a site where a bond is formed;

M is a linker represented by Formula 2;

$$\text{*-}X\text{-}L_2\text{-*} \qquad \text{[Formula 2]}$$

in which

* is a site where a bond is formed,

X is a cleavage site that is recognized by a caspase and which is cleavable thereby in hair papilla cells at a hair loss area, and $L_2$ is a linker, wherein $L_2$ is represented by Formula 5,

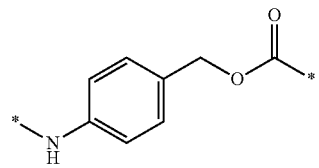

[Formula 5]

in which * is a site where a bond is formed; and

A is a drug for prevention or treatment of hair loss, wherein A is selected from the group consisting of finasteride, dutasteride and minoxidil.

2. The method according to claim 1, wherein the protein transduction domain is selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP).

3. The method according to claim 1, wherein W is at least one cysteine.

4. The method according to claim 1, wherein the cleavage site X is a peptide represented by SEQ ID NO: 4.

5. The method according to claim 1, wherein the linker $L_2$ is connected to an amine group of the drug for prevention or treatment of hair loss.

6. The method according to claim 1, wherein the drug for prevention or treatment of hair loss is finasteride or dutasteride, and the linker $L_2$ is connected to an amine group of the drug for prevention of treatment of hair loss.

7. The method according to claim 1, wherein the compound represented by Formula 1 is represented by Formula 7,

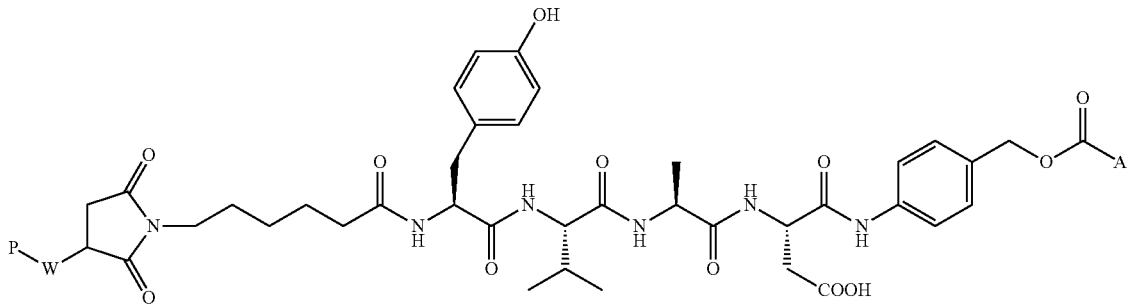

[Formula 7]

in which Formula 7,
P is a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP),
W is a direct bond or at least one amino acid, and
A is selected from the group consisting of finasteride, dutasteride and minoxidil.

8. The method according to claim 1, wherein the compound represented by Formula 1 is represented by Formula 9 or Formula 11,

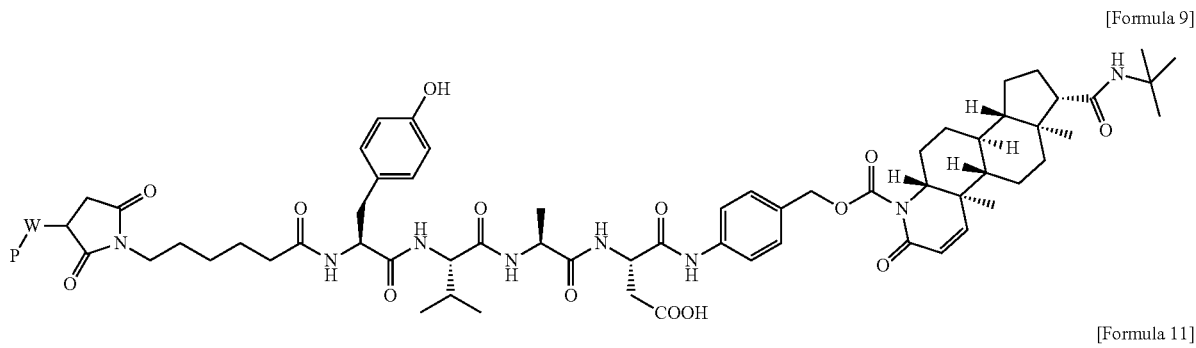

[Formula 9]

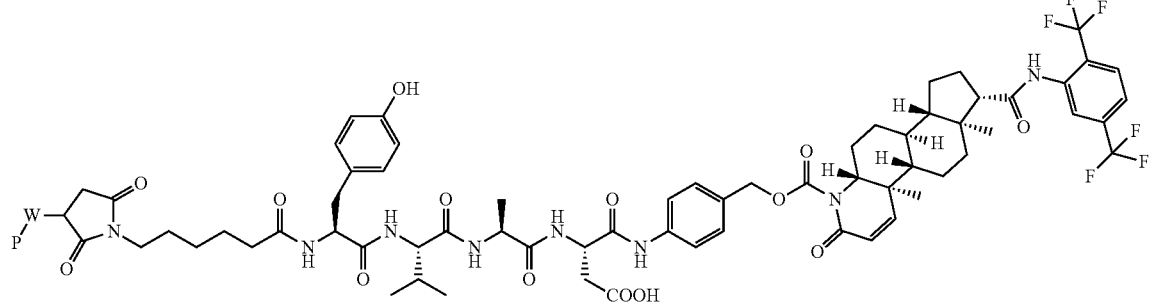

[Formula 11]

in which Formula 9 or Formula 11,
P is a protein transduction domain (PTD) selected from the group consisting of Hph-1, Mph-1, Sim-2, Tat, VP22, antennapedia (Antp), peptide-1 (Pep-1), protein transduction domain-5 (PTD-5), 11R, 7R, and cytoplasmic transduction peptide (CTP), and
W is at least one cysteine.

9. The method according to claim 1, further comprising administering to the target individual an effective amount of at least one selected from the group consisting of finasteride, dutasteride and minoxidil.

10. The method according to claim 1, further comprising administering to the target individual an effective amount of an anti-inflammatory agent.

11. The method according to claim 1, wherein the cleavage site X is a peptide.

* * * * *